United States Patent
Obermiller et al.

(10) Patent No.: US 9,572,556 B2
(45) Date of Patent: Feb. 21, 2017

(54) VOLUMETRIC GRAFTS FOR TREATMENT OF FISTULAE AND RELATED METHODS AND SYSTEMS

(75) Inventors: F. Joseph Obermiller, West Lafayette, IN (US); Michael C. Hiles, Lafayette, IN (US); Matthew R. Graham, Fort Wayne, IN (US); Clay D. Fette, Palm Beach Gardens, FL (US)

(73) Assignee: Cook Biotech Incorporated, West Lafayette, IN (US)

( * ) Notice: Subject to any disclaimer, the term of this patent is extended or adjusted under 35 U.S.C. 154(b) by 1129 days.

(21) Appl. No.: 11/415,403

(22) Filed: May 1, 2006
(Under 37 CFR 1.47)

(65) Prior Publication Data
US 2008/0004657 A1 Jan. 3, 2008

Related U.S. Application Data

(63) Continuation of application No. PCT/US2006/016748, filed on Apr. 29, 2006.
(Continued)

(51) Int. Cl.
*A61B 17/08* (2006.01)
*A61B 17/00* (2006.01)
*A61M 27/00* (2006.01)

(52) U.S. Cl.
CPC .. *A61B 17/0057* (2013.01); *A61B 2017/00004* (2013.01); *A61B 2017/00641* (2013.01); *A61B 2017/00654* (2013.01); *A61M 27/00* (2013.01)

(58) Field of Classification Search
CPC ................. A61B 17/0057; A61B 2017/00641; A61B 2017/00654; A61B 2017/00575
(Continued)

(56) References Cited

U.S. PATENT DOCUMENTS 2,127,903 A   8/1938   Bowen
4,511,653 A   4/1985   Play et al.
(Continued)

FOREIGN PATENT DOCUMENTS

EP   0 645 149   3/1995
EP   1 010 396   6/2000
(Continued)

OTHER PUBLICATIONS

Himpson, Rebecca C., et al. "Histological evidence for enhanced anal fistula repair using autologous fibroblasts in a dermal collagen matrix". Comparative Clinical Pathology, Apr. 2006, vol. 16, No. 1.
(Continued)

*Primary Examiner* — Gregory Anderson
*Assistant Examiner* — Sarah Simpson
(74) *Attorney, Agent, or Firm* — Woodard, Emhardt, Moriarty, McNett & Henry LLP

(57) ABSTRACT

Described are devices, methods, and systems useful in the treatment of fistulae, and in certain embodiments those having openings extending into the alimentary canal, such as anorectal fistulae. Illustratively, an anorectal fistula can be treated by placing a volumetric construct within the primary opening of the fistula. In certain embodiments, the volumetric construct can include a rolled remodelable material processed to form a substantially unitary body. Advantageous such remodelable materials can include collagenous extracellular matrix materials, such as small intestine submucosa.

45 Claims, 14 Drawing Sheets

Related U.S. Application Data

(60) Provisional application No. 60/676,118, filed on Apr. 29, 2005.

(58) Field of Classification Search
USPC .................................. 540/191; 606/191, 213
See application file for complete search history.

(56) References Cited

U.S. PATENT DOCUMENTS

| | | |
|---|---|---|
| 4,902,508 A | 2/1990 | Badylak et al. |
| 4,956,178 A | 9/1990 | Badylak et al. |
| 4,981,465 A | 1/1991 | Ballan |
| 5,192,301 A * | 3/1993 | Kamiya et al. ............... 606/213 |
| 5,192,302 A | 3/1993 | Kensey et al. |
| 5,219,576 A | 6/1993 | Chu et al. |
| 5,222,970 A | 6/1993 | Reeves |
| 5,275,826 A | 1/1994 | Badylak et al. |
| 5,281,422 A | 1/1994 | Badylak et al. |
| 5,304,123 A | 4/1994 | Atala et al. |
| 5,334,216 A * | 8/1994 | Vidal et al. ................... 606/213 |
| 5,374,261 A | 12/1994 | Yoon |
| RE34,866 E | 2/1995 | Kensey |
| 5,387,206 A | 2/1995 | Valentine et al. |
| 5,411,475 A | 5/1995 | Atala et al. |
| 5,423,777 A | 6/1995 | Tajiri et al. |
| 5,516,533 A | 5/1996 | Badylak et al. |
| 5,554,389 A | 9/1996 | Badylak et al. |
| 5,584,827 A | 12/1996 | Korteweg |
| 5,620,461 A | 4/1997 | Van De Moer |
| 5,628,762 A | 5/1997 | Al-Tameem |
| 5,643,305 A | 7/1997 | Al-Tameem |
| 5,752,974 A | 5/1998 | Rhee |
| 5,755,791 A | 5/1998 | Whitson et al. |
| 5,779,672 A | 7/1998 | Dormandy |
| 5,823,994 A | 10/1998 | Sharkey et al. |
| 5,824,054 A | 10/1998 | Khosravi et al. |
| 5,830,228 A | 11/1998 | Knapp et al. |
| 5,955,110 A | 9/1999 | Patel et al. |
| 5,993,485 A * | 11/1999 | Beckers ..................... 623/23.65 |
| 5,993,844 A | 11/1999 | Abraham et al. |
| 5,997,575 A | 12/1999 | Whitson et al. |
| 6,013,853 A * | 1/2000 | Athanasiou et al. ......... 424/423 |
| 6,090,996 A | 7/2000 | Li |
| 6,099,567 A | 8/2000 | Badylak et al. |
| 6,126,686 A | 10/2000 | Badylak et al. |
| 6,165,193 A | 12/2000 | Greene et al. |
| 6,200,336 B1 | 3/2001 | Pavcnik et al. |
| 6,206,931 B1 | 3/2001 | Cook et al. |
| 6,315,787 B1 | 11/2001 | Tsugita |
| 6,375,989 B1 | 4/2002 | Badylak et al. |
| 6,458,152 B1 | 10/2002 | Khosravi et al. |
| 6,569,081 B1 | 5/2003 | Nielsen |
| 6,623,509 B2 * | 9/2003 | Ginn ........................... 606/213 |
| 6,666,892 B2 | 12/2003 | Hiles et al. |
| 7,276,075 B1 | 10/2007 | Callas et al. |
| 7,645,229 B2 | 1/2010 | Armstrong |
| 8,083,768 B2 | 12/2011 | Ginn et al. |
| 2003/0013989 A1 | 1/2003 | Obermiller et al. |
| 2003/0036797 A1* | 2/2003 | Malaviya et al. ......... 623/14.12 |
| 2003/0051735 A1* | 3/2003 | Pavcnik et al. ............... 128/831 |
| 2003/0167088 A1 | 9/2003 | Abraham et al. |
| 2004/0158185 A1 | 8/2004 | Moran et al. |
| 2005/0013844 A1 | 1/2005 | Hadlock et al. |
| 2005/0049626 A1* | 3/2005 | Burgard ....................... 606/191 |
| 2005/0070759 A1 | 3/2005 | Armstrong |
| 2005/0090860 A1 | 4/2005 | Paprocki |
| 2005/0154446 A1 | 7/2005 | Phillips et al. |
| 2005/0155608 A1 | 7/2005 | Pavcnik et al. |
| 2005/0159776 A1 | 7/2005 | Armstrong |
| 2005/0182495 A1 | 8/2005 | Perrone |
| 2005/0222591 A1 | 10/2005 | Gingras et al. |
| 2006/0015142 A1 | 1/2006 | Malazgirt |
| 2007/0004961 A1 | 1/2007 | Case et al. |
| 2007/0198059 A1 | 8/2007 | Patel et al. |
| 2008/0004657 A1 | 1/2008 | Obermiller et al. |
| 2008/0027477 A1 | 1/2008 | Obermiller et al. |

FOREIGN PATENT DOCUMENTS

| | | |
|---|---|---|
| EP | 1 188 414 | 3/2002 |
| FR | 2 840 796 A1 | 12/2003 |
| RU | 2180529 C2 | 3/2002 |
| SU | 1718837 A1 | 3/1991 |
| SU | 1673130 A1 | 8/1991 |
| SU | 1690737 A1 | 11/1991 |
| WO | WO 98/11846 | 3/1998 |
| WO | WO 98/25637 | 6/1998 |
| WO | WO 00/19912 | 4/2000 |
| WO | WO 00/72759 A2 * | 12/2000 |
| WO | WO 03/009764 | 2/2003 |
| WO | WO 2005/020823 A1 | 3/2005 |
| WO | WO 2005/020847 | 3/2005 |
| WO | WO 2005/053547 | 6/2005 |
| WO | WO 2005/070302 | 8/2005 |
| WO | WO 2006/119256 | 11/2006 |
| WO | WO 2007/002260 A2 | 1/2007 |
| WO | WO 2007/011443 A2 | 1/2007 |
| WO | WO 2007/064819 A2 | 1/2007 |
| WO | WO 2007/090150 A2 | 8/2007 |
| WO | WO 2007/090155 A1 | 8/2007 |

OTHER PUBLICATIONS

Khairy, G. E. A., et al. "Percutaneous obliteration of duodenal fistula". J.R. Coll. Surg. Edinb., 45, Oct. 2000, 342-344.

Lisle, David A., et al. "Percutaneous Gelfoam Embolication of Chronic Enterocutaneous Fistulas: Report of Three Cases". Diseases of the Colon & Rectum, vol. 50, No. 2, Dec. 2006.

Maluf-Fiho, F. et al. "Endoscopic Treatment of Esophagogastric Fistulae with an Acellular Matrix." Gastrointestinal Endoscopy, Elsevier, NL, vol. 59, No. 5, Apr. 2004 (Apr. 2004), p. 151, XP004854594 abstract.

Moore, Robert D., et al. "Rectovaginal Fistula Repair Using a Porcine Dermal Graft". Obstetrics & Gynecology, 2004, 104, 1165-1167.

Schwesinger, Wayne H., "Management of Persistent Fistula After Gastrectomy" on-line question (www.medscape.com), posted on May 14, 2002.

Shah, A.M., et al. "Bronchoscopic closure of bronchopleural fistula using gelfoam" abstact. Journal of Association of Physicians of India, 2004, vol. 52 n JUIN, pp. 508-509.

Shaker MA, Hindy AM, Mounir RM, Geaisa KM. Egypt Dent J. Jul. 1995; 41(3): 1237-42.

Sheiman, Robert G., et al. "Percutaneous Treatment of a Pancreatic Fistula after Pancreaticoduodenectomy". J Vasc Interv Radiol, 2001, vol. 12, No. 4, pp. 524-526.

Shelton, Andrew A., et al. Transperineal Repair of Persistent Rectovaginal Fistulas Using an Acellular Cadaveric Dermal Grant (AlloDerm®). Diseases of the Colon & Rectum, Sep. 2006, vol. 49, No. 9.

U.S. Appl. No. 11/766,606, filed Jun. 6, 2007 to Obermiller et al.

Miklos, J. R., et al. "Rectovaginal Fistula Repair Utilizing a Cadaveric Dermal Allograft". International Urogynecology Journal, 1999, vol. 10, No. 6, pp. 405-406.

Schultz, David J., et al. "Porcine Small Instestine Submucosa as a Treatment for Enterocutaneous Fistulas". Journal of American College of Surgeons, 2002, vol. 194, No. 4, Apr. 2002, pp. 541-543.

Wilson Gunn on behalf of unnamed party, Letter to the European Patent Office, Jan. 30, 2007, pp. 1-4.

English Abstract of FR 840 796 A1 to Novatech Inc. Dec. 19, 2003, one page.

European Search Report and Written Opinion issued in European Patent Application No. 12171928.0 dated Jul. 21, 2014, five pages.

U.S. Appl. No. 12/793,030 to F. Joseph Obermiller et. al., Office Action mailed May 14, 2015.

U.S. Appl. No. 12/793,030 to Obermiller et al., Notice of Allowance mailed Sep. 17, 2015.

(56) References Cited

OTHER PUBLICATIONS

U.S. Appl. No. 12/793,030 to Obermiller et al., Response to Office Action filed Aug. 14, 2015.

* cited by examiner

VOLUMETRIC GRAFTS FOR TREATMENT OF FISTULAE AND RELATED METHODS AND SYSTEMS

REFERENCE TO RELATED APPLICATIONS

This application is a continuation of a PCT application entitled: VOLUMETRIC GRAFTS FOR TREATMENT OF FISTULAE AND RELATED METHODS AND SYSTEMS, Inventors: F. Joseph Obermiller, Michael C. Hiles, Matthew R. Graham, and Clay D. Fette, Application No. PCT/US2006/16748 filed Apr. 29, 2006, Express Mail Label No. EV 579025685US, and claims the benefit of priority of U.S. Provisional Patent Application Ser. No. 60/676,118 filed Apr. 29, 2005, both of which are incorporated herein by reference in their entirety.

BACKGROUND

The present invention resides generally in the field of devices and methods useful for treating fistulae, and in a particular aspect relates to the treatment of an anorectal fistula by filling its primary opening with a remodelable graft material.

As further background, a variety of fistulae can occur in humans and can occur for a variety of reasons, such as a congenital defect, inflammatory bowel disease, such as Chron's disease, irradiation, trauma, such as childbirth, or as a side effect from a surgical procedure. Fistulae that can occur in humans can include, for example, urethro-vaginal fistulae, vesico-vaginal fistulae, tracheo-esophageal fistulae, gastro-cutaneous fistulae, and any number of anorectal fistulae, such as recto-vaginal fistula, recto-vesical fistulae, recto-urethral fistulae, or recto-prostatic fistulae.

Anorectal fistulae can result from infection in the anal glands, which are located around the circumference of the distal anal canal which forms the dentate line. Approximately twenty to thirty such glands are found in humans. Infection in an anal gland usually results in an abscess, and the abscess can then track through or around the sphincter muscles into the perianal skin, where it can drain, either autonomously or via a surgical procedure. The tract that can result from the abscess is known as a fistula. The inner opening of the fistula, usually located at the dentate line, is known as the primary opening. The outer or external fistula opening is usually located in the perianal skin and is known as the secondary opening.

Anorectal fistulae can form a variety of pathways through the perianal tissue. For example, a fistula may take a take a "straight line" path from the primary to the secondary opening. This type of fistula is known as a simple fistula. Alternatively, a fistula may form multiple tracts ramifying from the primary opening and having multiple secondary openings. This type of fistula is known as a complex fistula.

The anatomic pathway that a fistula occupies can be classified according to its relationship to the anal sphincter muscles. The anal sphincter includes two concentric bands of muscle, the inner or internal sphincter muscle and the outer or external anal sphincter muscle. A fistula which passes between the inner and outer sphincter muscles is known as an inter-sphincteric fistula. A fistula that passes through both the internal and external sphincter muscles is known as a trans-sphincteric fistula, and a fistula that passes above both sphincter muscles is known as a supra-sphincteric fistula. A fistula that results from Crohn's disease usually ignores these anatomic planes, and is known as an extra-anatomic fistula.

Many complex fistulae consist of multiple tracts, some blind-ending and others leading to multiple secondary openings. One of the most common complex types of fistulae is known as a horseshoe fistula. In a horseshoe fistula, the infection can start in an anal gland (the primary opening) at the 12 o'clock location, for example, (with the patient in the prone position). From this primary opening, multiple fistulae can pass bilaterally around the anal canal, in a circumferential manner. Multiple secondary openings can occur anywhere around the periphery of the anal canal, thereby resulting in a fistula tract with a characteristic horseshoe configuration.

One technique for treating a perianal fistula includes excising a fistula from anal tissue by making an incision adjacent the anus that sufficiently contacts the fistula to ensure complete removal of the fistula. This surgical procedure tends to sever the fibers of the anal sphincter, and may cause incontinence.

Another surgical treatment for fistulae, known as a fistulotomy, involves passing a fistula probe through the tract of a fistula in a blind manner, guiding the probe primarily with only tactile sensation and experience. After passing the probe through the fistula tract, the overlying tissue can then be surgically divided and the fistula tract can then be allowed to heal. Because a variable amount of sphincter muscle can be divided during a fistulotomy, a fistulotomy may result in impaired sphincter control, and even frank incontinence.

Yet another technique for treating fistulae involves "coring-out" the tracts of one or more fistula, such as is described in U.S. Pat. Nos. 5,628,762 and 5,643,305. Unfortunately, however, these "coring-out" of procedures tend to make a fistula wider and more difficult to close. Additionally, the treatment of fistulae with surgical techniques, can lead to other potential complications, such as incontinence and multiple complex fistula formation.

In an alternative procedure, a fistula tract may be treated by inserting a seton, or a narrow diameter rubber drain through the fistula tract. The seton can be passed through the fistula tract and tied in a loop around the contained tissue and left for several weeks or months, thereby draining any infection from the area. This procedure is usually performed to mature the fistula tract prior to the performance of a more definitive closure procedure.

More recently, treatment methods have evolved which can include the injection of a sclerosant or a sealant, such as a collagen or fibrin glue, into a fistula tract in order to block and/or close the fistula. Glues used in these procedures can be very viscous and can clog the narrow channels of instruments used to deliver the sealants into the tract. The closure of a fistula with a sealant is usually performed as a two-stage procedure. The first stage includes the placement of a seton in the fistula to drain any infection that is within the fistula tract. The second stage, which usually occurs several weeks after the seton is placed, includes the injection of a suitable glue or other sealant within the tract of the fistula.

In view of this background, the need remains for improved and alternative techniques, devices, and systems useful for treating fistulae, such as anorectal fistulae. Certain aspects of the present invention are addressed to these needs.

SUMMARY

Accordingly, in one aspect, the present invention provides for the treatment of a fistula of the alimentary canal, such as an anorectal fistula, by filling its primary opening with a layered volumetric graft construct. The volumetric construct can include a rolled remodelable material that occupies a substantially unitary volume that can be shaped into a configuration that enhances closure of the primary opening.

In one aspect, the present invention provides a medical graft product for the treatment of an anorectal fistula. The medical graft product can include a rolled biocompatible sheet material that provides a volumetric body configured to fill a primary opening of an anorectal fistula.

In certain embodiments of the invention, a medical graft product is provided for the treatment of a fistula having a primary opening in the alimentary canal, a secondary opening, and a fistula tract extending therebetween. Such medical graft products comprise an elongate graft body of a remodelable matrix material, the elongate graft body including at least one generally conical longitudinal segment configured to lodge within and fill the primary fistula opening with remodelable extracellular matrix material. The elongate graft body is of a length sufficient to extend from the primary opening through the fistula tract and out the secondary opening when the generally conical segment is lodged within the primary opening. The generally conical longitudinal segment is comprised of rolled sheet-form extracellular matrix material and thereby defines spiral layers of the sheet-form extracellular matrix material. The spiral layers of sheet-form extracellular matrix material are sufficiently compact and bonded to one another to provide the generally conical longitudinal segment as a substantially unitary structure.

In yet another aspect, the present invention provides a medical graft product for the treatment of an alimentary (e.g. anorectal) fistula that includes an elongate plug. The elongate plug comprises a bioremodelable sponge form material and can occupy a volumetric shape that is adapted for deployment within a primary opening of the fistula.

In another aspect, the present invention provides a medical product for the closure of an anorectal or other alimentary fistula that includes a deployment sheath and a biocompatible graft body. The biocompatible graft body is configured for deployment through the sheath into a primary opening of the fistula so as to promote the closure of the fistula. Additionally, in certain aspects, the medical graft product includes a rolled fistula plug that is preloaded into a biocompatible sheath or cartridge that is suitable for traversing a tract of the fistula and deploying the plug for receipt in an opening of the fistula.

In still yet another aspect, the present invention provides a medical product for the treatment of an anorectal or other alimentary fistula that includes a remodelable material that occupies a volumetric shape and has at least two regions that are formed using differential drying techniques. The volumetric shape can be configured to substantially conform to a primary opening of the fistula so as to promote the closure and the healing of the fistula. Advantageous such remodelable materials can include extracellular matrix materials, such as mammalian small intestine submucosa.

In yet another aspect, the present invention provides a method for making a medical product useful for the treatment of an anorectal or other alimentary fistula. The method includes drying a rolled biocompatible sheet material contained within a mold so as to stabilize the material in a form configured for receipt in the fistula.

In another aspect, the present invention provides a method for treating an anorectal or other alimentary fistula that includes locating a rolled graft construct within a primary opening of the fistula so as to fill the opening.

In yet another aspect, the present invention provides a medical graft product for treating a fistula that includes a body comprising a rolled biocompatible sheet material providing a volumetric body configured to fill at least a portion of a fistula tract.

In another aspect, the present invention provides a medical graft product for the treatment of a fistula that includes a remodelable material having at least two regions formed by the differential drying of the remodelable material. The material can be configured to fill and promote the closure of the fistula opening. Advantageous such remodelable materials can include extracellular matrix materials, such as mammalian small intestine submucosa.

In yet another aspect, the present invention provides a fistula plug that can include a body comprising an extracellular matrix sponge form or foam material and occupying a shape that is adapted for receipt in at least a portion of a fistula tract.

In still yet another aspect, the present invention provides a medical graft product for treating a fistula that has a primary opening exposed to an alimentary canal and a fistula tract. The product comprises a porous graft body configured to lodge within and fill the primary opening. The body has a first portion that will be closer to and be more exposed to the alimentary canal than a second portion when the graft body is lodged in the primary opening. The first portion is less porous than the second portion.

In another embodiment, the present invention provides a method for treating a fistula having a primary opening and a fistula tract. The method comprises contacting tissue walls defining at least a portion of the opening or the tract with a flowable remodelable extracellular matrix material. In advantageous embodiments, the flowable material is delivered so as to at least substantially fill the opening and/or at least a portion of the fistula tract.

In another embodiment, the present invention provides a medical graft product useful for the treatment of a fistula having a primary opening. The medical graft product includes an elongate graft body of a resorbable matrix material, desirably a remodelable matrix material such as a remodelable ECM. The elongate graft body includes at least one longitudinal segment configured to lodge within and fill the primary opening, wherein the longitudinal segment is comprised of one or more pieces of compacted sheet-form matrix material defining contacting layer portions of the sheet-form matrix material. The contacting layer portions of sheet-form matrix material are sufficiently bonded to one another provide the longitudinal segment as a substantially unitary structure.

In another embodiment, the present invention provides a medical graft product for sealing an opening in a bodily organ or vessel, which includes an elongate graft body. The elongate graft body has at least one generally conical segment configured to lodge within and fill the opening. The longitudinal segment also has one or more pieces of compacted sheet-form collagenous matrix material defining contacting layer portions of the sheet-form collagenous matrix material, which are bonded to one another.

In another embodiment, the present invention provides a medical graft product for sealing an opening in a bodily organ or vessel that includes an elongate graft body. The elongate graft body includes at least one longitudinal segment having a generally circular cross-section and configured to lodge within and fill the opening. The longitudinal segment also includes one or more pieces of substantially randomly compacted sheet-form collagenous matrix material that defines contacting layer portions of the sheet-form collagenous material. The contacting layer portions are bonded to one another.

In another embodiment, the present invention provides a method of forming an implantable graft body. The method includes providing a mass of collagen-containing material to be dried to form a graft body, wherein the mass includes passages defined therein extending from a surface of the mass into the interior of the mass. The mass is then subjected to drying conditions. In doing so, the passages can enhance the drying process, e.g. by providing increased surface area extending into the interior regions of the mass that is exposed to the drying atmosphere. In certain embodiments, the mass is a frozen hydrated mass, and the drying conditions cause the sublimation of frozen water, such as in lyophilization processes. In such processes, the exposed passages extending into the mass can enhance the uniformity of the resulting lyophilized material. In some particular forms, methods for preparing graft bodies comprise: (i) providing a mold retaining a mass of collagen-containing material; (ii) creating a plurality of passages in the mass; (iii) hydrating the collagen-containing material mass; and (iv) drying the hydrated collagen-containing material mass in the mold with the displaced material volumes to form a dried graft body having dimensions generally defined by the mold. At least portions of the plurality of passages can be retained in the dried graft body. The collagen-containing material mass may be hydrated at any point during these methods, and in some forms, is hydrated before the passages are created. Also, in some aspects, the passages are created by displacing volumes of material in the collagen-containing material mass by forcing a plurality of material-displacing objects, e.g., needles, into the material mass. The mass can then be frozen, and the needles removed leaving the passages intact. The frozen mass can then be subjected to lyophilization drying conditions.

In another embodiment, the present invention provides a medical graft product for treating a fistula having at least a primary opening and a fistula tract. This medical graft product comprises an elongate plug body configured to lodge within and fill at least a segment of a fistula tract. The elongate plug body is comprised of a dried collagenous material and has a plurality of passages formed therein, wherein each of the formed passages extends from a plug body surface and into an interior region of the plug body, e.g. partially or completely through the body.

In another embodiment, the present invention provides a medical graft product for closing a fistula tract that includes an elongate tube structure having a body, a lumen, a proximal end, and a distal end. The elongate tube structure has a closed distal end, includes a remodelable material, and is sized and configured to reside within at least a segment of a fistula tract so as to provide for the closure of the fistula tract.

In another embodiment, the present invention provides a method for treating a fistula that includes locating a balloon within at least a segment of a fistula tract so as to facilitate closure of the fistula tract.

In another embodiment, the present invention provides a method for closing a fistula tract that includes providing an elongate remodelable and/or resorbable balloon. The balloon is associated with a lumen of a delivery device in a fashion wherein the balloon can be filled with a fill material driven through the lumen. In certain embodiments, at least a part of the balloon, and potentially all of the balloon, resides within the lumen, and is configured so as to be ejected from a distal opening of the lumen when a fill material is driven into a proximal opening of the lumen. In this manner, the distal lumen opening can be located at an opening to the fistula tract, or at some point within the fistula tract, and fill material driven through the lumen to deploy the balloon or portions thereof out of the lumen and into and along the fistula tract. In certain specific embodiments, the proximal balloon end is connected to the distal end of a delivery device, which also has a lumen and a proximal end. The balloon occupies a partially or completely inverted position within the lumen of the cannulated device. The proximal end of the delivery device can be positioned at or within to the primary or secondary opening of a fistula tract, and the balloon can be deployed within the fistula tract by adding fill material into the lumen of the delivery device so as to deploy the inverted balloon or balloon portions from the lumen into the fistula tract. The balloon can be further inflated within the fistula tract by continuing to fill the balloon with fill material to provide for the closure of the fistula tract. The present invention also provides related fistula closure systems including the balloon and associated delivery device.

Additional aspects of the invention relate to methods for treating fistulae which employ a medical graft product of the invention as described herein.

In other embodiments, the present invention provides medical products as discussed herein enclosed in sterile medical packaging.

The present invention provides improved and/or alternative methods, systems, and devices for treating anorectal fistulae and other bodily fistulae or similar undesired openings in organs or vessels. Additional embodiments as well as features and advantages of the invention will be apparent from the further descriptions herein.

DETAILED DESCRIPTION

Figure 1:
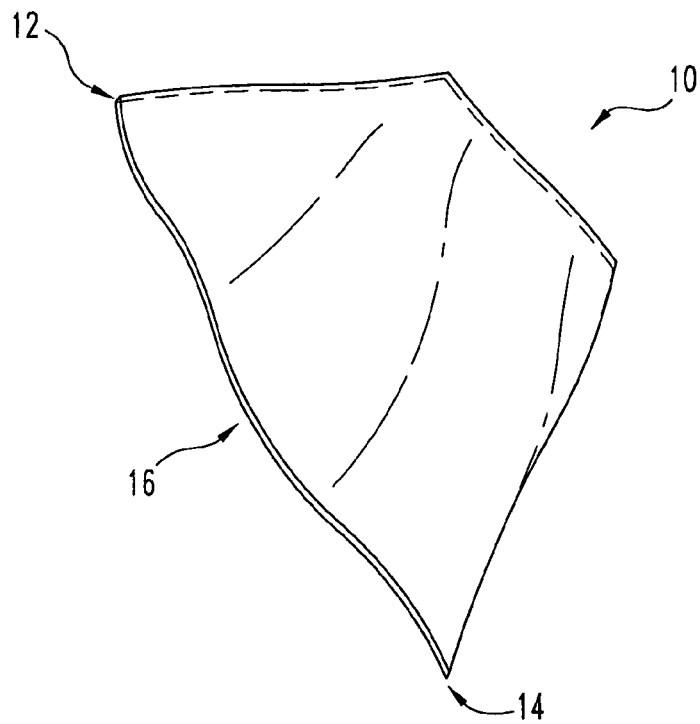
FIG. 1 depicts an illustrative sheet form material that can be useful in certain embodiments of the present invention.

For the purposes of promoting an understanding of the principles of the invention, reference will now be made to certain embodiments thereof and specific language will be used to describe the same. It will nevertheless be understood that no limitation of the scope of the invention is thereby intended, such alterations, further modifications and further applications of the principles of the invention as described herein being contemplated as would normally occur to one skilled in the art to which the invention relates.

As disclosed above, certain embodiments of the invention provide for the treatment of an anorectal or other bodily fistula by filling the primary opening of the fistula with a layered volumetric construct. Additionally, the volumetric construct can include a rolled remodelable material that occupies a substantially unitary volume. The unitary volume can be shaped into a configuration that enhances the closure of at least a primary opening of the fistula tract. In certain embodiments, a fistula plug can comprise an extracellular matrix material and can include certain adaptations which can enhance the deployment and securement of the fistula plug within a fistula tract.

Turning now to a discussion of graft materials, graft materials useful in certain embodiments of the present invention can include any suitable biocompatible material. Generally, the graft materials may include a remodelable material, such as a resorbable synthetic material or a naturally derived resorbable or remodelable material. Additionally, graft materials can include any other suitable naturally derived or any other suitable nonresorbable synthetic material, or any combination of any of the above such biocompatible materials. Such biocompatible materials that are at least bioresorbable will provide advantage in certain embodiments of the invention, with materials that are bioremodelable or otherwise tissue inductive so as to promote cellular invasion and ingrowth providing particular advantage. Illustratively, remodelable materials may be used in this context to promote cellular growth within the graft materials to promote healing and closure of at least the primary opening of an anorectal fistula.

Suitable materials for use in the invention can be provided by collagenous extracellular matrix (ECM) materials, including but not limited to those possessing biotropic or remodelable properties, including in certain forms angiogenic collagenous extracellular matrix materials. For example, suitable collagenous materials include ECM materials such as submucosa, renal capsule membrane, dermal collagen (including processed dermal collagen from human cadavers, which can be used as allograft in humans), dura mater, pericardium, facia lata, serosa, peritoneum, or basement membrane layers, including liver basement membrane. Suitable submucosa materials for these purposes include, for instance, intestinal submucosa, including small intestinal submucosa, stomach submucosa, urinary bladder submucosa, and uterine submucosa. The preferred medical graft products of the invention will include submucosa, such as submucosa derived from a warm-blooded vertebrate. Mammalian submucosa materials are preferred. In particular, submucosa materials derived from animals raised for meat or other product production, e.g. pigs, cattle or sheep, will be advantageous. Porcine submucosa provides a particularly preferred material for use in the present invention, especially porcine small intestine submucosa (SIS), more especially porcine small intestine submucosa retaining substantially its native cross-linking.

The submucosa or other ECM material can be derived from any suitable organ or other biological structure, including for example submucosa derived from the alimentary, respiratory, intestinal, urinary or genital tracts of warm-blooded vertebrates. Submucosa useful in the present invention can be obtained by harvesting such tissue sources and delaminating the submucosa from smooth muscle layers, mucosal layers, and/or other layers occurring in the tissue source. For additional information concerning submucosa useful in certain embodiments of the present invention, and its isolation and treatment, reference can be made, for example, to U.S. Pat. Nos. 4,902,508, 5,554,389, 5,993,844, 6,206,931, and 6,099,567.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

As prepared and used, the submucosa material or any other ECM material may optionally retain and/or otherwise include growth factors or other bioactive components native to the source tissue. For example, the submucosa or other ECM material may retain one or more growth factors such as basic fibroblast growth factor (FGF-2), transforming growth factor beta (TGF-beta), epidermal growth factor (EGF), and/or platelet derived growth factor (PDGF). As well, submucosa or other ECM material used in certain embodiments of the invention may retain or include other biological materials such as heparin, heparin sulfate, hyaluronic acid, fibronectin and the like. Thus, generally speaking, the submucosa or other ECM material may retain or otherwise include a bioactive component that induces, directly or indirectly, a cellular response such as a change in cell morphology, proliferation, growth, protein or gene expression. In certain preferred embodiments of the invention, the ECM material will exhibit the capacity to promote angiogenesis.

Further, in addition or as an alternative to the inclusion of such native bioactive components, non-native bioactive components such as those synthetically produced by recombinant technology or other methods, may be incorporated into the submucosa or other ECM material. These non-native bioactive components may be naturally-derived or recombinantly produced proteins that correspond to those natively occurring in the ECM material, but perhaps of a different species (e.g. human proteins applied to collagenous ECMs from other animals, such as pigs). The non-native bioactive components may also be drug substances. Illustrative drug substances that may be incorporated into and/or onto the ECM material can include, for example, antibiotics and/or thrombus-promoting substances such as blood clotting factors, e.g. thrombin, fibrinogen, and the like. These substances may be applied to the ECM material as a pre-manufactured step, immediately prior to the procedure (e.g. by soaking the material in a solution containing a suitable antibiotic such as cefazolin), or during or after engraftment of the ECM material within the patient.

Submucosa or other ECM material used in certain embodiments of the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. The ECM material used in certain embodiments of the invention is preferably disinfected with an oxidizing agent, particularly a peracid, such as peracetic acid. These and additional properties of submucosa or other ECM materials taught in U.S. Pat. No. 6,206,931 may be characteristic of the submucosa used in certain embodiments of the present invention.

Three-dimensionally stable porous matrix materials, such as resilient foam or sponge form materials, can be incorporated into graft constructs of the invention. Illustrative sponge or foam matrices will generally comprise porous, three-dimensionally stable bodies formed from suitable biocompatible matrix materials. For example, suitable biocompatible matrix materials include naturally-occurring polymers and/or synthetic polymers. More preferred sponge compositions of the invention will comprise collagen as a matrix-forming material, either alone or in combination with one or more other matrix forming materials. In general, sponge matrices useful in certain embodiments of the present invention can be formed by providing a liquid solution or suspension of a matrix-forming material, and causing the material to form a porous three-dimensionally stable structure; however, a sponge or foam material can be formed using any suitable formation method, as is known in the art.

Illustratively, in the formation of a collagenous sponge or foam material, a collagen solution or suspension can be prepared. The collagen may be derived from mammalian or other animal sources, for example, bovine, porcine or human sources, and desirably is derived from remodelable ECM materials as discussed herein. Synthetically-derived collagen may also be used. The determination of suitable collagen concentrations in the solution will be within the purview of those skilled in the art, with concentration ranges of about 0.05 g/ml to about 0.2 g/ml being typical.

Digestion of the collagen to form the collagen solution is usually carried out under acidic conditions, starting with ground, minced or otherwise comminuted collagen-containing tissue. Optionally, enzymatic digestion may be utilized using known enzymes for this purpose such as pepsin, trypsin, and/or papain. After digestion, the enzymes can be removed by suitable, known techniques.

The collagenous solution and/or suspension can be employed as a moldable or castable material in the formation of the foam or sponge. The cast material can be dried directly without chemical crosslinking or can be crosslinked with a suitable crosslinking agent and then dried. Illustrative crosslinking agents for these purposes include glutaraldehyde, formaldehyde, carbodiimides, UV irradiation, or other crosslinking agents. In preferred embodiments of the invention, the crosslinking agent will contain polar groups that impart a hydrophilic character to the final sponge matrix material. Desirably, a polyepoxide crosslinker is utilized for this purpose, especially a polyglycidyl ether compound. Suitable such compounds include ethylene glycol diglycidyl ether, available under the trade name Denacol EX810 from Nagese Chemical Co., Osaka, Japan, and glycerol polyglycidyl ether available under the trade name Denacol EX313 also from Nagese Chemical Co. Typically, polyglycidyl ethers or other polyepoxide compounds utilized in the invention will have from 2 to about 10 epoxide groups per molecule. The use of such epoxides and/or other crosslinking agents which impart polar groups and a hydrophilic character to the resulting matrix will provide for good wettability and rapid hydration and expansion of closure devices of the invention.

Preferred sources of collagen for forming sponge matrices useful in certain embodiments of the invention include extracellular matrix materials such as collagenous submucosal tissues, and other collagenous basement membrane materials. These include, for example, small intestinal submucosa, stomach submucosa, urinary bladder submucosa, liver basement membrane, and other basement membrane materials. For additional information as to these collagenous matrix materials and their preparation, reference can be made for example to U.S. Pat. Nos. 4,511,653, 4,902,508, 4,956,178, 5,554,389, and 6,099,567, and International Publication Nos. WO9825637 and WO9822158, each of which is hereby incorporated herein by reference in its entirety. In forming sponge matrices, these materials are preferably processed and utilized under conditions which retain their favorable growth properties. This may include, for example, processing under conditions in which native proteins and/or other materials, for instance biotropic agents, are retained in their bioactive form. For example, the collagen sources, and resulting sponge matrices, may include active native substances such as one or more growth factors, e.g. basic fibroblast growth factor (FGF-2); transforming growth factor beta (TGF-beta); epidermal growth factor (EFG); platelet derived growth factor (PDGF); and/or other substances such as glycosaminoglycans (GAGs); and/or fibronectin (FN).

Sponge matrix materials that can be used to form illustrative devices of the invention can be highly expandable when wetted, so as to achieve an expanded configuration. Illustratively, expandable sponge materials can exhibit the capacity to expand at least 100% by volume, more preferably at least about 200% by volume, and typically in the range of about 300% by volume to about 1000% by volume, when wetted to saturation with deionized water. Sponge materials used in the invention can also exhibit advantageous rates of expansion, achieving volume expansions as noted above in less than about 10 seconds, more preferably less than about 5 seconds, when immersed in deionized water.

Highly compact, dense sponge matrices can be prepared by first hydrating or otherwise wetting a porous sponge matrix, and then compressing and drying the element. Such preparative processes generally provide a more dense, rigid and stably compressed sponge matrix than processes such as simple compaction of the dry sponge matrix. Drying can be conducted sufficiently to stabilize the sponge matrix. For example, preferred drying procedures will reduce the liquid (e.g. water) content of the matrix to less than about 20% by weight, more preferably less than about 10% by weight. Compression forces can be applied so as to achieve a final density and/or desirable configuration, and can be applied in one, two or three dimensions, including radially. The drying of the compacted element can involve lyophilization (or freeze drying) or vacuum drying at ambient or elevated temperatures. When processed in this fashion, upon removal of the compaction force, the sponge matrix is stabilized structurally and remains in its highly dense and compacted state until contacted with a liquid susceptible to absorption by the matrix, for example body fluids. The pores of the matrix are thereby stably retained at a volume substantially reduced from their maximum volume, but return to a partially or fully expanded state when the matrix material is wetted.

Compressed sponge matrices forming graft bodies of the invention can be highly dense, typically having densities of at least about 0.05 g/cm$^3$, preferably in the range of about 0.05 g/cm$^3$ to about 0.2 g/cm$^3$, and more preferably about 0.075 g/cm$^3$ to about 0.2 g/cm$^3$. The compacted sponge matrix can have sufficient rigidity to be deployed by passage through needles, catheters or sheaths, for example by utilizing a push rod or other pusher element to force the sponge matrix graft body through the needle and/or catheter cannula. Expanded sponge densities (dry) will generally be less than the corresponding compacted densities. Typical expanded densities (dry) will range from about 0.01 g/cm$^3$ to about 0.1 g/cm$^3$, more preferably about 0.02 g/cm$^3$ to about 0.07 g/cm$^3$.

Compressed sponge materials may also contain agents which promote further retention of the compressed, high density form of the matrices. These may include for example starch, cellulose, sugars such as dextrose, or glycerin. Such agents can optionally be included in the liquid (preferably aqueous) used to hydrate or otherwise wet the sponge prior to compaction and drying. For additional information concerning foam or sponge form materials that can be useful in certain embodiments of the present invention, reference can be made, for example, to U.S. Pat. App. Pub. No. 2003/0013989.

In additional embodiments, fistula treatment devices of the invention can be made from ECM's or other collagenous materials that have been subjected to processes that expand the materials. In certain forms, such expanded materials can be formed by the controlled contact of an ECM material with one or more alkaline substances until the material expands, and the isolation of the expanded material. Illustratively, the contacting can be sufficient to expand the ECM material to at least 120% of (i.e. 1.2 times) its original bulk volume, or in some forms to at least about two times its original volume. Thereafter, the expanded material can optionally be isolated from the alkaline medium, e.g. by neutralization and/or rinsing. The collected, expanded material can be used in any suitable manner in the preparation of a graft device. Illustratively, the expanded material can be enriched with bioactive components, dried, and/or molded, etc., in the formation of a graft construct of a desired shape or configuration. In certain embodiments, a dried graft construct formed with the expanded ECM material can be highly compressible (or expandable) such that the material can be compressed for delivery, such as from within the lumen of a cannulated delivery device, and thereafter expand upon deployment from the device so as to become anchored within a patient and/or cause closure of a tract within the patient.

Expanded collagenous or ECM materials can be formed by the controlled contact of a collagenous or ECM material with an aqueous solution or other medium containing sodium hydroxide. Alkaline treatment of the material can cause changes in the physical structure of the material that in turn cause it to expand. Such changes may include denaturation of the collagen in the material. In certain embodiments, it is preferred to expand the material to at least about three, at least about four, at least about 5, or at least about 6 or even more times its original bulk volume. The magnitude of the expansion is related to several factors, including for instance the concentration or pH of the alkaline medium, exposure time, and temperature used in the treatment of the material to be expanded.

ECM materials that can be processed to make expanded materials can include any of those disclosed herein or other suitable ECM's. Typical such ECM materials will include a network of collagen fibrils having naturally-occurring intramolecular cross links and naturally-occurring intermolecular cross links. Upon expansion processing as described herein, the naturally-occurring intramolecular cross links and naturally-occurring intermolecular cross links can be retained in the processed collagenous matrix material sufficiently to maintain the collagenous matrix material as an intact collagenous sheet material; however, collagen fibrils in the collagenous sheet material can be denatured, and the collagenous sheet material can have an alkaline-processed thickness that is greater than the thickness of the starting material, for example at least 120% of the original thickness, or at least twice the original thickness.

Illustratively, the concentration of the alkaline substance for treatment of the remodelable material can be in the range of about 0.5 to about 2 M, with a concentration of about 1 M being more preferable. Additionally, the pH of the alkaline substance can in certain embodiments range from about 8 to about 14. In preferred aspects, the alkaline substance will have a pH of from about 10 to about 14, and most preferably of from about 12 to about 14.

In addition to concentration and pH, other factors such as temperature and exposure time will contribute to the extent of expansion, as discussed above. In this respect, in certain variants, the exposure of the collagenous material to the alkaline substance is performed at a temperature of about 4 to about 45° C. In preferred embodiments, the exposure is performed at a temperature of about 25 to about 40° C., with 37° C. being most preferred. Moreover, the exposure time can range from at least about one minute up to about 5 hours or more. In some embodiments, the exposure time is about 1 to about 2 hours. In a particularly preferred embodiment, the collagenous material is exposed to a 1 M solution of NaOH having a pH of 14 at a temperature of about 37° C. for about 1.5 to 2 hours. Such treatment results in collagen denaturation and a substantial expansion of the remodelable material. Denaturation of the collagen matrix of the material can be observed as a change in the collagen packing characteristics of the material, for example a substantial disruption of a tightly bound collagenous network of the starting material. A non-expanded ECM or other collagenous material can have a tightly bound collagenous network presenting a substantially uniform, continuous surface when viewed by the naked eye or under moderate magnification, e.g. 100× magnification. Conversely, an expanded collagenous material can have a surface that is quite different, in that the surface is not continuous but rather presents collagen strands or bundles in many regions that are separated by substantial gaps in material between the strands or bundles when viewed under the same magnification, e.g. about 100×. Consequently, an expanded collagenous material typically appears more porous than a corresponding non-expanded collagenous material. Moreover, in many instances, the expanded collagenous material can be demonstrated as having increased porosity, e.g. by measuring for an increased permeability to water or other fluid passage as compared to the non-treated starting material. The more foamy and porous structure of an expanded ECM or other collagenous material can allow the material to be cast or otherwise prepared into a variety of sponge or foam shapes for use in the preparation of medical materials and devices.

It can further allow for the preparation of constructs that are highly compressible and which expand after compression. Such properties can be useful, for example, when the prepared graft construct is to be compressed and loaded into a deployment device (e.g. a lumen thereof) for delivery into a patient, and thereafter deployed to expand at the implant site.

After such alkaline treatments, the material can be isolated from the alkaline medium and processed for further use. Illustratively, the collected material can be neutralized and/or rinsed with water to remove the alkalinity from the material, prior to further processing of the material to form a graft construct.

A starting ECM material (i.e., prior to treatment with the alkaline substance) can optionally include a variety of bioactive or other non-collagenous components including, for example, growth factors, glycoproteins, glycosaminoglycans, proteoglycans, nucleic acids, and lipids. Treating the material with an alkaline substance may reduce the quantity of one, some or all of such non-collagenous components contained within the material. In certain embodiments, controlled treatment of the remodelable material with an alkaline substance will be sufficient to create a remodelable collagenous material which is substantially devoid of nucleic acids and lipids, and potentially also of growth factors, glycoproteins, glycosaminoglycans, and proteoglycans.

In certain embodiments, one or more bioactive components, exogenous or endogenous, for example, similar to those removed from an expanded material during alkaline processing, can be returned to the material. For example, an expanded material can include a collagenous material which has been depleted of nucleic acids and lipids, but which has been replenished with growth factors, glycoproteins, glycosaminoglycans, and/or proteoglycans. These bioactive components can be returned to the material by any suitable method. For instance, in certain forms a tissue extract, such as is discussed in U.S. Pat. No. 6,375,989 which is hereby incorporated herein by reference in its entirety, containing these components can be prepared and applied to an expanded collagenous material. In one embodiment, the expanded collagenous material can be incubated in a tissue extract for a sufficient time to allow bioactive components contained therein to associate with the expanded collagenous material. The tissue extract may, for example, be obtained from non-expanded collagenous tissue of the same type used to prepare the expanded material. Other means for returning or introducing bioactive components to an expanded remodelable collagenous material include spraying, impregnating, dipping, etc. as known in the art. By way of example, an expanded collagenous material may be modified by the addition of one or more growth factors such as basic fibroblast growth factor (FGF-2), transforming growth factor beta (TGF beta), epidermal growth factor (EGF), platelet derived growth factor (PDGF), and/or cartilage derived growth factor (CDGF). As well, other biological components may be added to an expanded collagenous material, such as heparin, heparin sulfate, hyaluronic acid, fibronectin and the like. Thus, generally speaking, an expanded collagenous material may include a bioactive component that induces, directly or indirectly, a cellular response such as a change in cell morphology, proliferation, growth, protein or gene expression.

Expanded collagenous materials can be used to prepare a wide variety of fistula plug devices. Methods for preparing such plug devices can include contacting an ECM or other collagenous starting material with an alkaline substance in an amount effective to expand the material, casting or otherwise forming the expanded collagenous material into a plug shape (e.g. one of those described herein), and lyophilizing the expanded material to form a dried plug device Turning now to a discussion of certain synthetic materials that can be incorporated into illustrative graft products and methods of the invention, such synthetic materials can include nonresorbable synthetic biocompatible polymers, such as cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or mixtures or copolymers thereof. Illustrative resorbable synthetic materials can include polylactic acid, polyglycolic acid or copolymers thereof, a polyanhydride, polycaprolactone, polyhydroxy-butyrate valerate, polyhydroxyalkanoate, or another biodegradable polymer or mixture thereof. For further information concerning suitable synthetic materials (both biodegradable and nonbiodegradable), useful in certain embodiments of the present invention, reference can be made, for example, to U.S. Utility Patent Application Pub. No. 2005/0228486 titled, "Implantable Frame with Variable Compliance," filed on Apr. 11, 2005 ("Express Mail" Mailing Label No. EV 327 135 804 US), which claims priority to U.S. Provisional Patent Application titled, "Implantable Frame with Variable Compliance," filed on Apr. 13, 2004. Such synthetic materials can be used to form fistula plug devices as described herein, either alone or in combination with ECM or other collagenous materials herein identified.

Turning now to a general discussion of medical graft products useful in certain embodiments of the invention and certain methods for making and using the same, illustrative graft products can be formed into any suitable volumetric shape or space-filling configuration that is suitable for promoting closure of at least a primary opening of a fistula, such as an anorectal fistula. Illustratively, graft products of the invention can be formed by folding or rolling, or otherwise overlaying one or more portions of a biocompatible material, such as a biocompatible sheet material. In certain embodiments, the overlaid biocompatible sheet material can be compressed and dried or otherwise bonded into a volumetric shape such that a substantially unitary construct is formed. The substantially unitary construct can then be placed in a fistula in a manner such that the construct fills at least the primary opening of the fistula, a portion of the fistula tract, and/or the secondary fistula opening.

With reference now to FIG. 1, an illustrative medical graft product can be constructed by providing an ECM sheet material that has a trapezoidal shape 10. In certain embodiments, the sheet material 10 can include a single ECM layer. If desirable, the single layer can be formed by fusing or otherwise bonding a plurality of smaller ECM segments or strips to form a single sheet material having a larger surface area. Illustratively, for example, suitable bonding can include compressing overlapping areas of smaller ECM strips under dehydrating conditions.

In alternative embodiments, the ECM sheet material 10 can comprise a multilaminate ECM material. Illustratively, the multilaminate ECM material can be formed by bonding a plurality of stacked and/or substantially overlapping ECM layers together. In certain embodiments, such multilaminate ECM materials can include from one to about ten or more layered ECM segments, arranged or layered in a partially or completely overlapping manner, such as a crisscross and/or crosshatch or other suitable arrangement or pattern. Alternatively, a multilaminate ECM material can include a single ECM segment that is folded or loosely rolled over itself one or more times. Optionally, an adhesive, glue, or any other suitable bonding agent, such as are discussed in more detail below, may be placed between ECM layers to achieve a partial or complete bond. For more information concerning formation of collagenous sheet material that can be useful in certain embodiments of the present invention, reference can be made, for example to U.S. Pat. Nos. 2,127,903, 5,755,791, 5,955,110, 5,997,575, 6,206,931, and/or 6,666,892 and/or International Publication No. WO96/32146, dated Oct. 17, 1996, publishing International Application No. PCT/US96/04271, filed Apr. 5, 1996.

Figure 2:
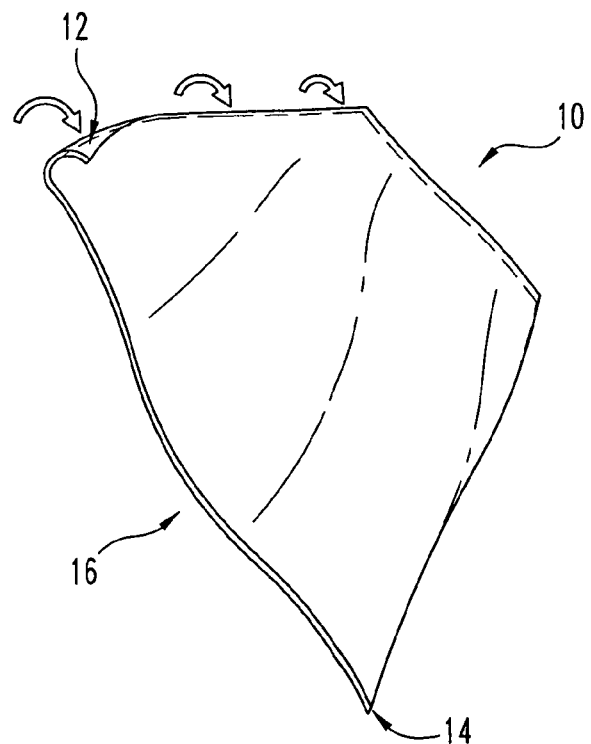
FIG. 2 depicts an illustrative sheet form material that can be useful in certain embodiments of the present invention.
Figure 3:
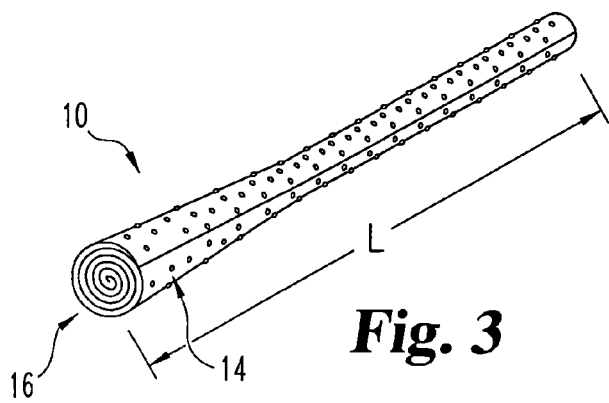
FIG. 3 depicts an illustrative sheet form material that can be useful in certain embodiments of the present invention.

Referring now to FIGS. 2 and 3, in certain embodiments the trapezoidal ECM sheet material 10 can be hydrated with a suitable hydrant, such as sterilized water or saline, and rolled into a suitable volumetric shape, such as a cone for example (see FIG. 3). Illustratively, as is depicted in FIG. 2, the trapezoidal sheet material 10 can be rolled from corner 12 to corner 14 along the longest base 16 of the trapezoid so as to naturally create a conical structure with the rolled material 10 (see FIG. 3). Additionally, in alternative embodiments, the direction of the roll can be varied in order to adjust the taper of the construct, as well as each terminal diameter of the construct. Still further, the sheet material can be rolled around a mandrel and subsequently processed so as to impart a lumen through the graft construct, such as for delivery of the construct over a wire guide or other elongate delivery guide member.

Figure 4A:
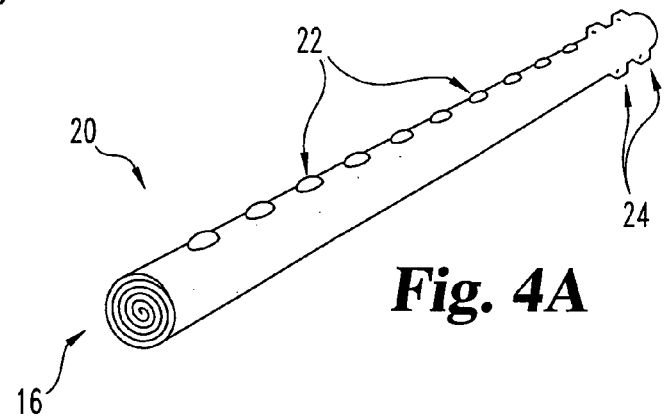
FIG. 4A depicts an illustrative medical graft product that can be useful in certain embodiments of the present invention.
Figure 4B:
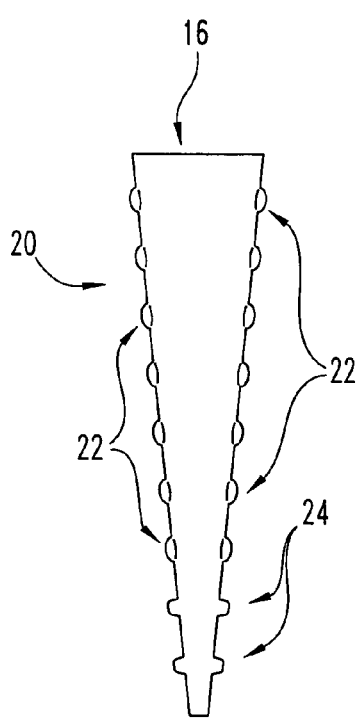
FIG. 4B depicts an illustrative medical graft product that can be useful in certain embodiments of the present invention.

Illustratively, once the sheet material 10 has been rolled, the overlapping spirally wound layers of the sheet material 10 can be bonded together to form a substantially unitary medical graft product 20 (see FIGS. 4A and 4B). Any suitable bonding technique, as is known in the art and/or discussed below can be used to unify the ECM sheet material 10. One such illustrative bonding technique can include lyophilization, which is discussed in more detail below, of the rolled sheet material 10. In certain embodiments, the hydrated sheet material 10 can be lyophilized while contained within a conically shaped mold or form. The mold can be sized such that it presses the layers of the spirally wound sheet material together while the material dries. Alternatively, however, the mold can be sized to only sufficiently support the sheet material in a spirally wound configuration during drying, if desirable.

Additionally, in certain embodiments, the mold can include a plurality of apertures or holes that can extend through a wall of the mold, thereby providing access to the conical cavity of the mold from an extra-atmospheric location. These apertures can serve to enhance the drying of the rolled sheet material during the lyophilization process. Illustratively, the mold apertures can also be configured to provide surface protuberances 22 formed on the unitary graft construct 20, as are shown in FIGS. 4A and 4B (see also proturbances or nibs 22 on construct 10, FIG. 3), which can in turn serve to facilitate securement of the resulting graft bodies, and/or to remove epithelial cells (de-epithelialize) or otherwise abrade surfaces of the fistula opening(s) or tracts to facilitate healing, or provide other desirable handling characteristics. Further, in certain embodiments, the mold can be configured to form a spool or dumb-bell type structure 24 at the proximal end of the graft construct 20. Illustratively, the spooled section 24 can be used to assist with placement of the graft 20 within a fistula tract, such as for example, by winding or otherwise attaching or locating a string or suture within the spool 24 and thereafter using the suture to pull the graft 20 proximally through the tract, as is discussed in further detail below. Additionally, in certain embodiments, the spools corresponding with the spooled section 24 can illustratively condition or otherwise roughen or de-epithelialize the tract tissue so as to enhance the ingrowth of patient tissue into an illustrative remodelable graft construct.

Further, other such suitable bonding techniques can include any suitable dehydrothermal crosslinking method and/or any other suitable drying method, such as evaporative cooling and/or vacuum pressing, and/or any combination of such suitable drying methods. Additionally, bonding can occur or be assisted by placing a suitable bonding material or agent between the layers of the rolled construct, such as before the sheet material is rolled, for example, and/or by soaking or contacting at least a portion of the rolled construct with a suitable bonding agent. Suitable bonding agents can include, for example, collagen gels or pastes, gelatin, or other agents including reactive monomers or polymers, such as cyanoacrylate adhesives for example. As well, bonding can be facilitated using chemical cross-linking agents, such as glutaraldehyde, formaldehyde, epoxides, genipin or derivatives thereof, carbodiimide compounds, polyepoxide compounds, or other similar agents. Cross-linking of ECM materials may also be catalyzed by exposing the matrix to UV radiation, by treating the collagen-based matrix with enzymes such as transglutaminase and lysyl oxidase, and by photocrosslinking. Additionally, bonding may be achieved by combining any two or more of the above bonding agents or methods.

Turning now to a more complete discussion of drying techniques that can be useful in certain embodiments of the invention, lyophilization can include providing an ECM material that contains a sufficient amount of hydrant such that the voids in the material matrix are filled with the hydrant. The hydrant can comprise any suitable hydrant known in the art, such as purified water or sterile saline, or any suitable combination thereof. Illustratively, the hydrated material can be placed in a freezer until the material and hydrant are substantially in a frozen or solid state. Thereafter, the frozen material and hydrant can be placed in a vacuum chamber and a vacuum initiated. Once at a sufficient vacuum, as is known in the art, the frozen hydrant will sublime from the material, thereby resulting in a dry remodelable material.

In alternative embodiments, a hydrated ECM material can be lyophilized without a pre-freezing step. In these embodiments, a strong vacuum can be applied to the hydrated material to result in a rapid evaporative cooling which freezes the hydrant within the ECM material. Thereafter, the frozen hydrant can sublime from the material thereby drying the ECM material. Desirably, an ECM material that is dried via lyophilization maintains a substantial amount of the void space, or open matrix structure that is characteristic of the harvested ECM material.

Drying by evaporation, or air drying, generally comprises drying a partially or completely hydrated remodelable material by allowing the hydrant to evaporate from the material. Evaporative cooling can be enhanced in a number of ways, such as by placing the material in a vacuum, by blowing air over the material, by increasing the temperature of the material, by applying a blotting material during evaporation, or by any other suitable means or any suitable combination thereof. Unlike lyophilization, the amount of void space or open matrix structure within an ECM material is diminished during evaporative drying.

Drying by vacuum pressing generally comprises compressing a fully or partially hydrated remodelable material while the material is subject to a vacuum. One suitable method of vacuum pressing comprises placing a remodelable material in a vacuum chamber having collapsible walls. As the vacuum is established, the walls collapse onto and compress the material until it is dry. Similar to evaporative drying, when a remodelable material is dried in a vacuum press, more of the material's open matrix structure is diminished or reduced than if the material was dried by lyophilization.

Turning now to a discussion of material properties, remodelable materials having an open matrix structure exhibit some different material properties than remodelable materials having a more diminished or collapsed matrix structure. For example, a material having an open matrix structure is soft and readily compliant to an implant site. In contrast, a material having a more collapsed matrix structure tends to be more stiff or rigid, more durable, and have greater compliance, or shape memory than a material with a more open matrix structure. Additionally, a remodelable material having a smaller pore size or more collapsed matrix can serve to promote fluid segregation or differentiation between bodily cavities that are spanned by the remodelable material of diminished matrix structure.

Additionally, the rate and amount of tissue growth in and/or around a remodelable material are controlled by several factors. One such factor includes the amount of open space available in the material's matrix structure for the infusion and support of a patient's cell building components, such as fibroblasts. Therefore, an open matrix structure provides for quicker, and sometimes more, growth of patient tissue in the remodelable material. This increased rate of patient tissue growth in the remodelable material can lead to quicker remodeling of the material by patient tissue.

Turning now to a discussion of differential drying methods, certain differential drying methods can be used to make illustrative graft constructs that are desirably configured for placement with fistulae. These differential drying methods generally include drying a remodelable material, under vacuum, wherein a portion of the material contains a frozen hydrant, while other regions of the material contain hydrant in liquid form, or alternatively, frozen hydrant that is converted to liquid form during the drying process. Any suitable method or device may be used to control the physical state of hydrant in the remodelable material during drying, such as, for example, a temperature control device, or, use of thermodynamic means, such as covering or shielding a portion of the material subject to vacuum, with a suitable shielding material, such as a material of sufficient porosity to induce differential drying.

Further, an illustrative fistula plug that comprises a remodelable material and is differentially dried can comprise at least two regions having differing properties and porosities. These differing regions can be established in certain locations or comprise a certain arrangement or pattern within the remodelable fistula plug. This arrangement or pattern can be selected in order to promote or achieve any one of a number of desirable results, such as, for example, enhancing inter-layer bonding within the remodelable construct or within the sheet material used to roll the illustrative construct, differing the rate and/or ability of patient tissue to infiltrate or invade certain regions of a construct, increasing the compliance and/or durability of the remodelable construct, and/or enhancing the ability of at least a portion of the fistula plug to maintain independence between bodily cavities. Additionally, the arrangement or pattern can be selected to promote or achieve combinations of any of the previous desirable results.

In certain embodiments, differential drying can include shielding portions or regions of a sufficiently hydrated ECM graft construct and thereafter providing a vacuum around the shielded material. The uncovered portions of the ECM material can dry via lyophilization under vacuum, as discussed above. The shielded regions can dry over time in these conditions as well. In these embodiments, the resulting ECM material can include a dry remodelable material having a somewhat open matrix structure that corresponds with the unshielded regions, while having a more diminished or collapsed matrix structure that corresponds to the shielded regions.

It is advantageous in some differential drying techniques to perform drying operations under relatively mild temperature exposure conditions that can minimize deleterious effects upon the ECM materials used in certain embodiments of the invention, for example native collagen structures and potentially bioactive substances present. Thus, drying operations conducted with no or substantially no duration of exposure to temperatures above human body temperature or slightly higher, say, no higher than about 38° C., will preferably be used in some forms of the present invention.

Figure 5:
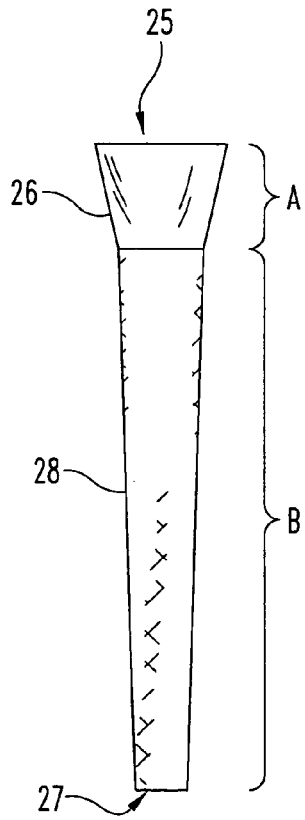
FIG. 5 depicts an illustrative medical graft product that can be useful in certain embodiments of the present invention.

Turning now to a discussion of certain medical graft products of the invention and certain methods and systems for producing the same, with reference to FIG. 5, depicted is a fistula plug 25, formed with an ECM material that can be used to block an anorectal fistula. The plug 25 can include a head 26 and can occupy a conical tail 28 that terminates in a truncated tip 27. Additionally, the plug 25 can have two regions of differing porosity that can be created using any suitable differential drying technique, as discussed above. For example, as depicted in FIG. 5, the head 26 of the plug 25 can occupy a region A that comprises a matrix structure that is more diminished than the matrix structure of the region B that corresponds to the tail 27 of the plug 25.

In an illustrative forming procedure, the depicted plug 25 can be formed by rolling or otherwise layering a hydrated ECM material into a conical shape. Thereafter, the hydrated material can be compressed within a suitable mold having a shape that is similar to the plug 25 geometry that is depicted in FIG. 5. In certain embodiments, the mold can have differing regions, such as differing porosity regions, which can establish the differing matrix regions A,B of the graft construct 25 during a suitable drying and/or compression technique. Illustratively, the mold porosity of region A can be sufficient to result in the collapse of the ECM matrix structure in region A during a suitable drying technique. Additionally, the mold porosity of region B can be sufficient to maintain the open matrix structure of the remodelable material during a suitable drying technique, e.g. lyophilization. During the illustrative drying technique or techniques, the ECM layers can dehydrothermally bond in order to provide a substantially unitary construct 25, having a suitable length L, as is discussed in more below.

Illustratively, the fistula plug 25 that is depicted in FIG. 5 can be used, in certain embodiments, to fill or otherwise close an anorectal fistula. The plug can be placed such that the more diminished porosity region A resides in the primary opening of the fistula while the more open porosity region B resides in at least a portion of the fistula tract. In this configuration, the diminished matrix region A can help isolate the fistula tract from the rectum while the more open matrix region B serves to promote more rapid closure of the fistula with its desirable remodeling properties.

Figure 6:
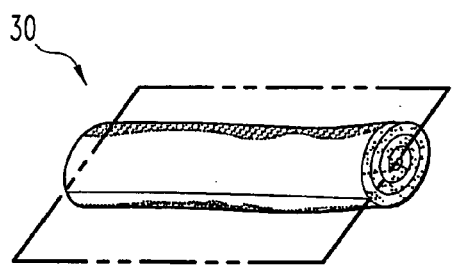
FIG. 6 depicts an illustrative medical graft product that can be useful in certain embodiments of the present invention.

Turning now to FIG. 6, an illustrative fistula plug that occupies a cylindrical volume is shown. The depicted plug 30 can be formed by rolling a hydrated rectangular ECM sheet material and thereafter pressing and drying the construct to form a substantially unitary cylindrical construct 30. Illustratively, the spirally wound layers of the construct 30 can become dehydrothermally bonding during pressing and drying of the hydrated material. Additionally, in certain embodiments, one or more cuts can be imparted to certain portions of the bonded cylindrical plug 30 that can enhance the expansive ability of the plug after it is located within a patient and/or provide strain relief to the plug 30 in order to enhance the resistance of the plug 30 to backing out of the fistula tract after emplacement occurs. For example, certain body motion, such as repetitive motion (standing up/sitting down or exercise) can cause an implanted device to migrate, e.g. back out, in the absence sufficient flexibility of the overall device and/or sufficient device fixation or anchoring. In some inventive variants, graft plugs useful for treating fistulas as described herein will incorporate cuts or other adaptations along their length to provide strain relief to the plug and increase its ability to bend or flex along its longitudinal axis under a given load. Illustratively, the cuts can run longitudinally down the entire length of and/or only a portion of the entire length of the plug 30, and/or can extend across the body of the plug 30 at any desirable angle or angles. The cuts can occupy any depth that is suitable to desirably enhance the expansion of the plug 30 within a lumen of the patient and/or provide adequate strain relief.

Figure 7:
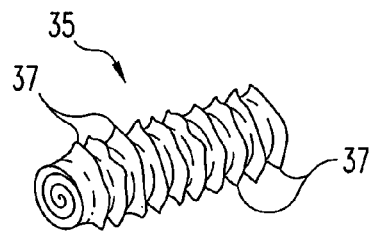
FIG. 7 depicts an illustrative medical graft product that can be useful in certain embodiments of the present invention.

With reference now to FIG. 7, a cylindrical fistula plug 35 is shown that can be configured for use in closing or otherwise filling a bodily fistula. As is depicted, the fistula 35 can be formed having a plurality of protuberances or ribs 37 or other suitable anchoring or expansive means that can extend from the bodily surface of the plug 35. In certain embodiments, the protuberances 37 can be integral to the plug 7, such as by being imparted to the plug 7 during a bonding or drying process, from a suitable compression mold for example. Alternatively, the protuberances 37 can be imparted to the plug 35 after the plug is formed, such as by removing or otherwise cutting suitable portions of the plug in order to form the protuberances. In certain embodiments, the protuberances and intervening narrower portions of the plug along with length can provide a volumetric plug with integrated strain relief for enhanced flexibility.

Additionally, the plug 35 can be constructed to occupy any suitable diameter and/or any suitable length to fill any suitable bodily fistula. For example, the diameter of the plug 35 can be altered by varying the compression that is imparted to the construct during a suitable drying procedure and/or by varying the amount of sheet material used to form the construct, such as by varying the overall size of the sheet material, e.g. the number of turns, and/or by varying the thickness of the sheet material used, e.g. the number of multilaminate layers that can form the sheet material. Illustratively, the length of the construct 35 can be varied by either appropriately sizing the sheet material and/or trimming the construct to the desired length after inter-layer bonding is achieved, for example. In certain embodiments, the plug 35 can be custom built to fit a specific fistula in a specific patient, if desirable.

Figure 8:
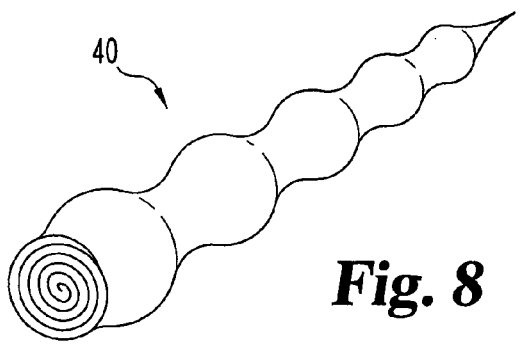
FIG. 8 depicts an illustrative medical graft product that can be useful in certain embodiments of the present invention.

Turning now to FIG. 8, shown is another illustrative fistula plug 40 that can be useful in certain embodiments of the present invention. The plug 40 can have a conical shape and can further include a plurality of bulges, such as symmetrical bulges, disposed along the length of the plug 40. In certain embodiments, the bulges can occupy any suitable geometric configuration and/or frequency and can serve to assist in the securement of the plug 40 within a bodily fistula. Additionally, the bulges or reliefs can be imparted or formed into the construct to such a degree to impart sufficient strain relief and flexibility to the construct to help resist migration after it is emplaced within a patient.

Figure 9:
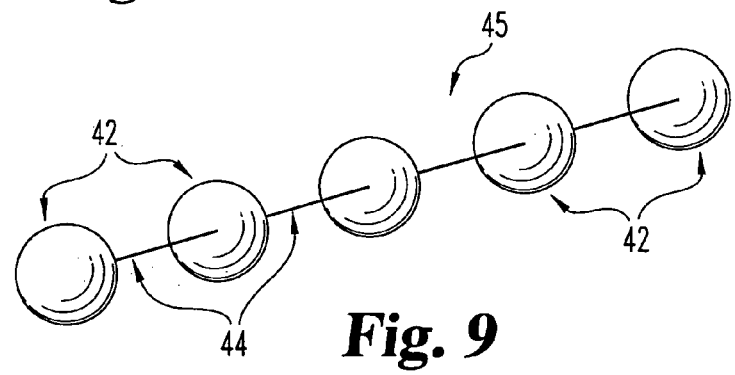
FIG. 9 depicts an illustrative medical graft product that can be useful in certain embodiments of the present invention.
Figure 10:
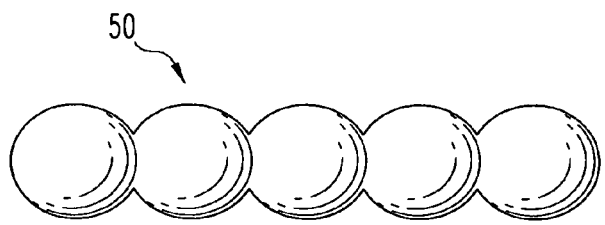
FIG. 10 depicts an illustrative medical graft product that can be useful in certain embodiments of the present invention.
Figure 11:
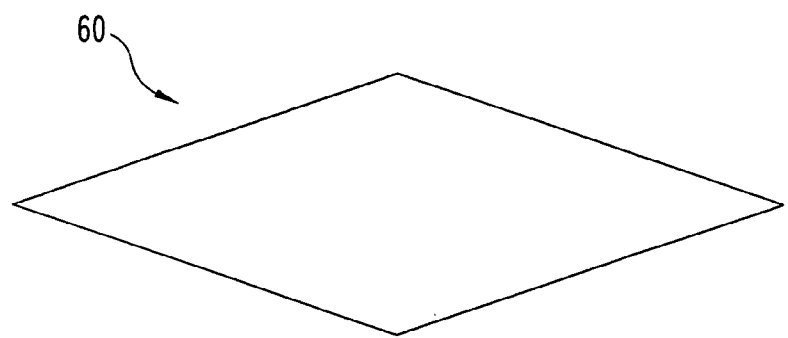
FIG. 11 depicts an illustrative medical graft product that can be useful in certain embodiments of the present invention.

With general reference now, to FIGS. 9 through 11, a remodelable foam or sponge form material can be used in the construction of illustrative fistula plugs of the invention. As discussed above, illustrative sponge form devices will advantageously be highly expandable when wetted, so as to achieve an expanded configuration. Preferred sponge materials of the invention will also exhibit advantageous rates of expansion, achieving volume expansions as noted above in less than about 10 seconds, more preferably less than about 5 seconds, when immersed in deionized water. In certain embodiments, sponge form fistula blockers or plugs may be formed individually by compaction/drying of an appropriately sized sponge element, or they may be individually excised from a larger compacted/dried sponge matrix.

For example, in certain embodiments, illustrative graft constructs having highly compact, dense sponge matrices can be prepared by first hydrating or otherwise wetting a porous sponge matrix, and then compressing and drying the element into the desired plug configuration or volumetric shape. Drying can be conducted sufficiently to stabilize the sponge matrix. Compression forces can be applied so as to achieve a final density and/or desirable volumetric configuration, and can be applied in one, two or three dimensions, including radially. The drying of the compacted element can involve lyophilization (or freeze drying) or vacuum drying at ambient or elevated temperatures. When processed in this fashion, upon removal of the compaction force, the sponge matrix is stabilized structurally and the volumetric graft construct will remain in its highly dense and compacted state until contacted with a liquid susceptible to absorption by the matrix, for example body fluids. The pores of the matrix are thereby stably retained at a volume substantially reduced from their maximum volume, but return to a partially or fully expanded state when the matrix material is wetted.

More specifically now, with reference to FIG. 9, an illustrative graft construct 45 can include five sponge form spheres 42 that can be connected to one another with a continuous suture line 44, illustratively comprising a resorbable material, that can penetrate the center of each sphere. Illustratively, the spheres 42 can be located at any suitable distance from one another and can occupy any suitable. diameter, as is desirable to close or otherwise fill one or more fistula openings and/or tracts. In certain embodiments, the suture line 44 can be secured through each sphere after each sphere is formed, using illustrative techniques disclosed above, or, alternatively, each sphere or ball 42 can be formed around the suture 44 by locating the suture 44 within each mold that can be used to form each sphere, for example. Additionally, any suitable number of spheres 42 can be used to form the graft construct 45, and any suitable device or material can be used to unite or connect each sphere 42 of the graft construct 45. By connecting each sponge sphere with a length of thread or other filamentous material, strain relief is also imparted to the graft construct. In certain aspects, this strain relief is desirable to help prevent migration of the device within the patient. The amount of provided strain relief can be modified by varying the amount of length between each sphere at emplacement and/or by varying the diameter and/or material of construction of one or more spheres or interconnecting filaments of the construct.

Turning now to FIG. 10, another illustrative graft construct 50 is shown. The graft construct 50 can be comprised of ECM based sponge material that is compressed within a mold having the shape of the cross-sectional view of a rope. The resulting graft construct 50 can be highly expansive when wetted, which can desirably enhance the ability of the graft construct 50 to close or fill the primary opening of a fistula. In illustrative procedures, a suitable hydrant, such as saline, may be applied or delivered to the graft construct 50 after it is located in a primary fistula opening to enhance the expansion of the construct within the fistula tract. Alternatively, or additionally, a bodily fluid of the patient can sufficiently wet the located graft construct 50 so as to promote the expansion of the construct 50 within the fistula. The amount of strain relief provided within the device can be changed by varying the ratio of the diameter of the construct along its length, e.g. center of rope strand to rope strand edges, as well as by varying the overall diameter of the construct.

With reference now to FIG. 11, another medical graft product 60 that can be useful in certain embodiments of the present invention is shown. Illustratively, the medical graft product can occupy an oblong or elongated symmetrical diamond shape. The medical graft product 60 can be comprised of any suitable biocompatible material, such as a rolled synthetic material that is bonded and compressed or pressed into the volumetric shape depicted in FIG. 11. In alternative embodiments, the medical graft product can be formed into a shape similar to that of a bow tie having a smaller center section and wider ends. Such formation can be facilitated, if desirable, by the compressive wrapping, tying, or bonding of additional material, e.g. graft sheet material or sutures, near the longitudinal center of the device.

Turning now to further discussion concerning the securement of an illustrative fistula plug of the invention within a fistula tract, any suitable anchoring means can be used to enhance or maintain the placement of an illustrative fistula plug within a targeted fistula tract or portion thereof, such as the primary opening. In certain embodiments, anchoring means can include suitable barbs or other protuberances or ribs as are known in the art and/or as are discussed herein. As well, suitable anchoring means can include one or more sutures, in certain illustrative configurations, to anchor illustrative graft constructs of the invention within fistulae, as is discussed in further detail below (see text accompanying FIGS. 13A through 14B). In certain aspects, one or more sutures can be located in either the head of the plug and/or the plug tail and securely passed through adjacent patient tissues in order to provide for the securement of the plug within the tract. In additional aspects, the expansive force of the plug, e.g. a sponge form plug, can be sufficient to provide for the securement of the plug within at least the primary opening of the tract.

In one operative method for treating an anorectal fistula, a fistula probe or other elongate tracking device can be passed through a fistula tract from the secondary opening to a position outside the primary opening in order to identify the primary opening. If desirable, a hydrogen peroxide solution can be injected through the tract from the secondary opening to assist in finding the primary opening. After the primary opening is identified, the fistula probe can be removed and more hydrogen peroxide solution can be injected through the tract, such as by injecting the solution from a syringe placed at the secondary opening. Thereafter, the probe can be re-inserted within the tract and a seton or suture can be attached to the distal end of the probe and thereafter be pulled from the primary opening through the tract and out the secondary opening. Further irrigation can thereafter occur, if desirable, while the seton or thread is in place, for example. In certain aspects, the seton can then be removed and another suture can be passed through the tract from the secondary opening to the primary opening, leaving a distal suture end beyond the primary opening and a proximal suture end extending out of the secondary opening. The passage of the suture can for example be accomplished by attaching an end of the suture to the distal end of a fistula probe, and passing the probe from the secondary to the primary opening). After detachment of the distal suture end from the probe and withdrawal of the probe, the distal end of the suture can then be tied to the plug, e.g. around the plug body or secured through a hole adjacent the plug's leading end. Using the suture, the plug can then be pulled through the tract from the primary opening to the secondary opening until the plug fits snuggly within the tract. The trailing plug end wedged in the primary opening can then be trimmed if needed, and the trailing plug end can be secured to patient tissues, such as with one or more Z sutures passing through the plug and through the internal sphincter or other tissues at or around the location of the primary opening. This securement at the primary opening site will desirably also draw adjacent patient tissues over the trailing plug end to cover the same, so that no or substantially no amount of the plug remains exposed to the intestinal tract. Thereafter, the secondary plug end can be trimmed and sutured or otherwise secured to the patient, desirably also with no amounts of the plug exposed beyond the secondary opening. It will of course be understood that many variations in such a treatment protocol can be contemplated, including for instance the use of filaments other than sutures or passed devices (e.g. forceps or probes with gripping or other plug-engagement adaptations) to pull the plug through the primary opening and into the fistula tract. As well, these or other protocols can be adapted to pass a plug in the opposite direction, i.e. from the secondary opening to the primary opening, to as to fill some or all of the tract and plug the primary opening. It will thus be understood that these described protocols illustrate certain treatment methods of the invention but are not otherwise limiting thereof.

Additionally, in illustrative embodiments, one or more anchors, barbs, ribs, protuberances, and/or other suitable surface modifications can be incorporated on and/or within an illustrative plug to roughen, condition, or otherwise de-epithelialize at least a portion of the fistula tract, such as the primary opening, during and/or after emplacement of the graft within the tract. The conditioning of the tract tissue can serve to initiate a localized healing response in patient tissue that can be advantageous in enhancing the ingrowth of patient tissue into an illustrative plug construct, such as a plug comprising an ECM material. Further, in illustrative embodiments, where a suture, leader, or string is used to assist with the emplacement of an illustrative graft construct within a tract, as is discussed below, the leader can comprise an abrasive material, or comprise one or more sections and/or surface features and/or adaptations, e.g. one or more bristles that can directionally emanate from the leader material and that can serve to roughen or otherwise condition or de-epithelialize patient tissue upon travel through and/or location within a fistula tract.

Figure 12:
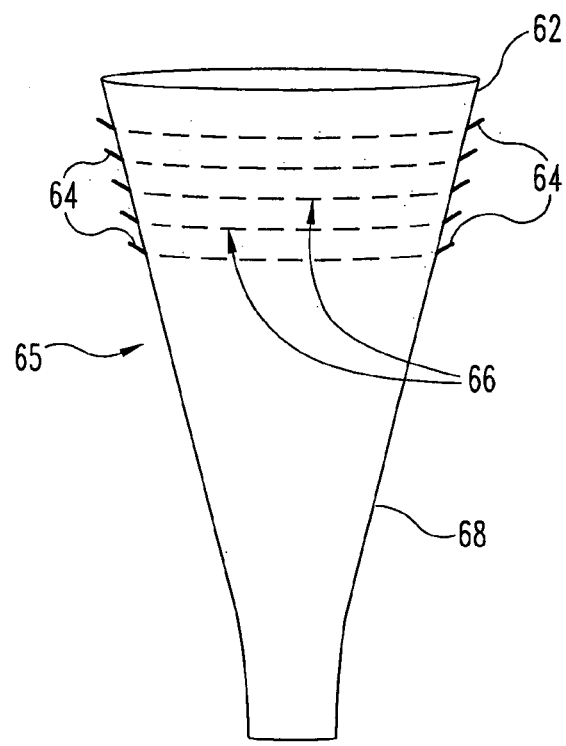
FIG. 12 depicts an illustrative medical graft product that can be useful in certain embodiments of the present invention.

With reference now to FIG. 12, for example, illustrative anchoring and/or tissue conditioning devices 64 can be formed by locating a plurality of sutures 66 through the head portion 62 of an illustrative construct 65 in a manner such that each suture end 64 extends from the surface of the construct's head portion 62 to form a plurality of anchoring whiskers 64. As shown, each suture end or whisker 64 can be angled in a directional manner to inhibit the head portion 62 of the construct from backing out of a primary fistula opening.

Additionally, in certain embodiments, whiskers or bristles 64 can be located throughout the entire surface of the construct 65, or, alternatively, throughout only the tail portion 68 of the construct, or, still alternatively, only in certain isolated portions of the construct 65. Illustratively, whiskers 64 can extend from the entire circumference of the construct 65, or only certain portions thereof, as well as exit the construct's surface at any desirable angle, such as a 90 or 45 degree angle, in any suitable direction (e.g. toward the head or toward the tail). In certain embodiments, for example, a variety of whiskers 64 can depart from the graft's 65 surface at a plurality of angles and/or directions in a plurality of regions on the graft's 65 surface. Illustratively, in certain embodiments, one or more whiskers, comprised of an absorbable or remodelable suture material, for example, can serve to provoke a sustained de-epithelialization of patient tissue after a remodelable graft is implanted, thereby enhancing the remodelablility of the graft, as well as the absorption or remodeling of the one or more whiskers. For more information concerning suitable barbs and/or tissue conditioning devices that can be useful in certain embodiments of the present invention, reference can be made, for example, to U.S. Pat. App. Pub. Nos. 2003/0013989, 2005/0049626, 2005/0070759 and/or U.S. utility patent application titled "Implantable Graft to Close a Fistula," filed on Jan. 21, 2005 ("Express Mail" Mailing Label No. EV 314 907 725).

Turning now to additional discussion concerning locating and delivering illustrative medical graft constructs of the invention into or within certain bodily fistulae, any suitable delivery method or placement technique can be used to locate one or more illustrative medical graft products within one or more bodily fistulae or portions thereof, such as at least the primary opening.

Illustratively, a plug can be located within a fistula by pulling the tail or proximal end of the plug through the primary opening in a manner such that the head portion or distal end of the plug fills the primary fistula opening and the tail fills at least a portion of the fistula tract. In certain embodiments, the fistula plug can be pulled through the fistula tract using a fistula probe or a suitable pair of surgical hemostats. Alternatively, an illustrative plug can be pulled through a primary opening using a suitable leader, such as suture. In still alternative embodiments, an illustrative plug can be deployed within a fistula tract through a suitable biocompatible sheath, catheter, or needle, optionally configured to traverse the tract of a fistula and optionally located within the fistula tract over a suitable wire guide or under endoscopic guidance. In these embodiments, an illustrative plug construct can be deployed in an over the wire configuration or through an unobstructed sheath lumen (see e.g. FIG. 16, which depicts an illustrative graft device having a central lumen for receiving wire guide).

Additionally, in illustrative embodiments, any suitable method can be used to prepare the tract, such as remove any infection and/or any undesirable tissue or debris from the fistula tract before a medical graft product is deployed within the fistula. Any suitable means can be used to remove infection and/or debris, including the implantation of a seton and/or flushing the tract using a fistula probe or any other suitable flushing means, and/or any suitable combination thereof. Suitable such flushing or tract preparation can include contacting the tract with an aqueous medium, e.g. hydrogen peroxide or saline, one or more antibiotics or other desirable drugs, and/or one or more sclerosive agents. For more information concerning placement of illustrative medical constructs within fistulae and related fistulae flushing methods and techniques, reference can be made, for example, to U.S. Pat. App. Pub. Nos. 2003/0013989, 2005/0049626, 2005/0070759 and/or U.S. utility patent application titled "Implantable Graft to Close a Fistula," filed on Jan. 21, 2005 ("Express Mail" Mailing Label No. EV 314 907 725).

With general reference now to FIGS. 13A through 14B, shown are illustrative graft constructs of the invention that contain a string adaptation or leader which can assist in the deployment and securement of the illustrative graft constructs. Illustratively, the string can be used as a leader that charts a pathway through a fistula in need of closure. For example, in certain embodiments, the string or suture can be pulled through an anorectal fistula tract using a fistula scope, or alternatively can be pulled through the fistula tract with a previously located wire guide. After the string is located within the tract, in certain embodiments, the string can be attached at any suitable location on an illustrative fistula plug (such as the spool 24 portion of the illustrative plug construct 20 in FIGS. 4A and 4B) and can thereafter be used to pull the tail of the plug trough the primary opening, thereby filling the primary opening with at least the head of the plug. Such suitable points of string attachment can include, for example, the head of the device, such as in combination with a plate that can be used to drive the plug through the tract, and/or at the tail of the device, and/or at locations that are integral to the device body, such as being contained within the body of the plug, such as by tracking back and forth through the body in a zigzag type fashion or pattern.

Additionally, in certain embodiments, for example, the string can first be used as a seton that is left in place within the fistula for a period of time that is sufficient to drain and/or clean the fistula tract. Thereafter, the string can be tied to a fistula plug and used as a leader in an illustrative plug deployment procedure. In alternative embodiments, a string can be attached to an illustrative plug and then located within a fistula tract so as to deploy the plug within the tract, or, in yet still alternative embodiments, a string leader can be used to pull a plug into a fistula tract through a secondary opening, if desirable.

In illustrative embodiments, after the leader is used to sufficiently locate a suitable plug within a tract, the string can be removed from the fistula plug, such as with cutting shears, for example. In alternative embodiments, the string or suture can be made from a remodelable or otherwise resorbable material such that the string or suture can be left in place within the fistula tract. In these embodiments, the resorbable or remodelable leader can be used to anchor to secure the plug within the tract such as by being tied to patient tissue at any suitable location, such as a location just inside or external to the secondary fistula opening. Further, in alternative embodiments, an illustrative fistula plug can be positioned within a fistula tract so as to span the entire length of the tract from the primary opening to a location external to the secondary opening. In these embodiments, the string or suture can be used to secure the tail of the plug to patient tissue at an external location.

Figure 13A:
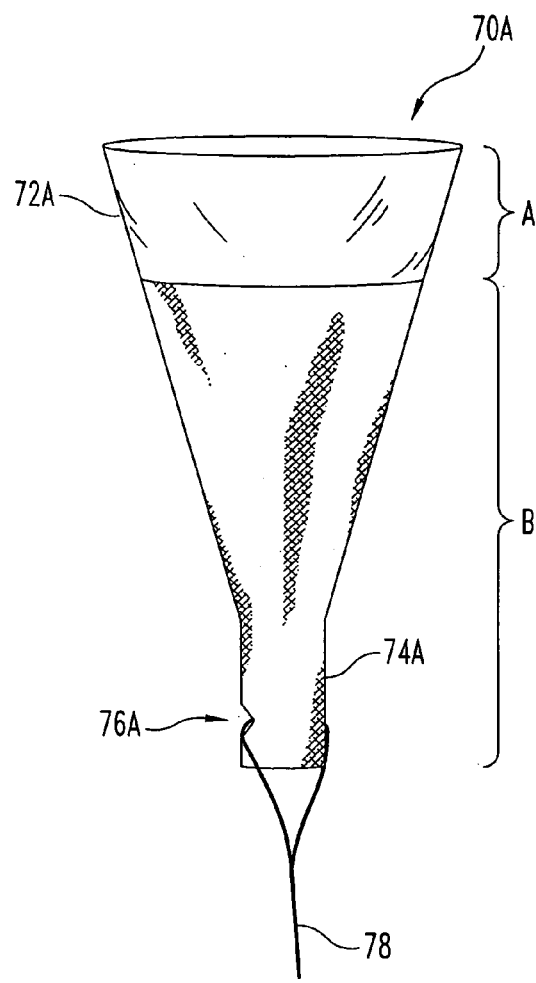
FIG. 13A depicts an illustrative medical graft product that can be useful in certain embodiments of the present invention.

More specifically now, with reference to FIG. 13A, an illustrative fistula plug 70A is shown having a head portion 72A and a tail portion 74A, wherein the head portion 72A occupies a matrix structure A that differs from the matrix structure B in the tail portion 74A. Additionally, the illustrative plug 70A has an indentation 76A at the proximal end of the tail that can be used, in certain embodiments, for the attachment of a string leader 78 that can be used to pull the plug 70A through a primary opening of a fistula.

Figure 13B:
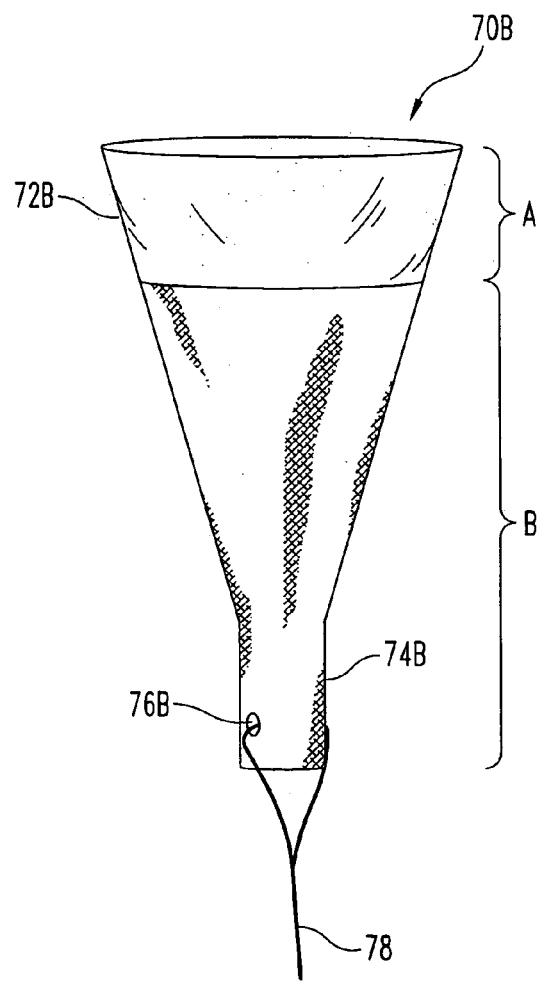
FIG. 13B depicts an illustrative medical graft product that can be useful in certain embodiments of the present invention.

Turning now to FIG. 13B, an illustrative embodiment is depicted wherein the tail portion 74B of a graft construct 70B includes an aperture 76B that extends transversely through the proximal tail 74B portion of the graft 70B. Illustratively, the aperture 76B can be used for the receipt of a suture or string 78. Additionally, the string can be passed through a fistula tract and then tied through the aperture 76B of the plug 70B so as to provide a mechanism for locating the plug 70B within a fistula tract. After the plug is sufficiently located, the string can be removed, by trimming the tail of the plug 70B, for example, or can be used to secure the plug within the fistula.

Figure 14A:
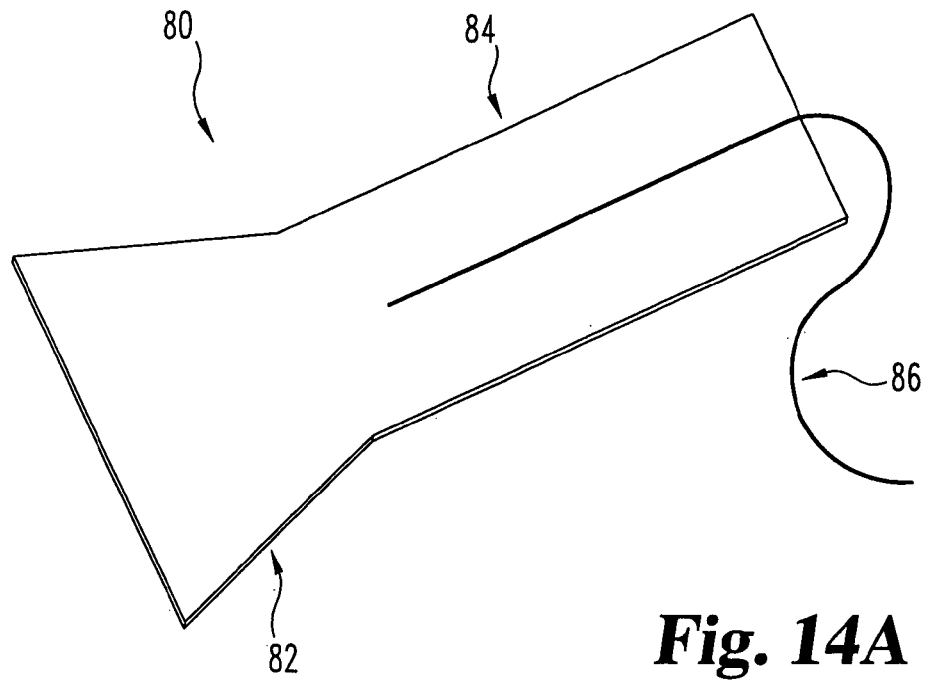
FIG. 14A depicts an illustrative sheet form material that can be useful in certain embodiments of the present invention.
Figure 14B:
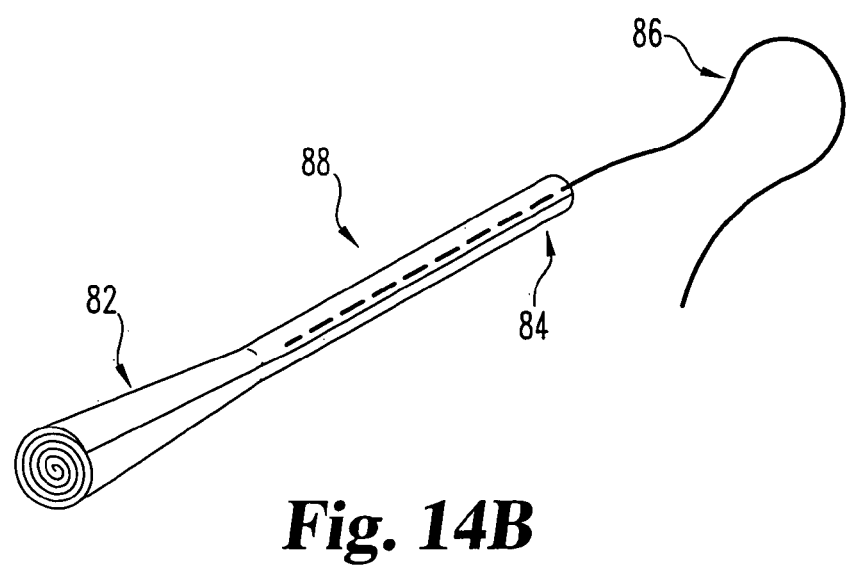
FIG. 14B depicts an illustrative medical graft product that can be useful in certain embodiments of the present invention.

With reference now to FIGS. 14A and 14B, depicted is an illustrative device 88 of the invention that has a conical head portion 82 and an extended cylindrical tail portion 84 that is configured to extend entirely through a lengthy fistula tract from the primary opening to a position external to the secondary opening. Additionally, the illustrative device 88 can include a leader 86 that can be used to assist in the placement of the device 88 within the tract. FIG. 14A depicts a suitable sheet material 80 configuration that can be used to form the illustrative extended device 88. Additionally, as is shown in FIG. 14A, the leader can be incorporated within the device 88 by being rolled within, and optionally bonded and/or compressed within, the spirally wound layers of sheet material 80. Illustratively, after the construct is placed within a suitable fistula, the head 82 and/or tail 84 portions can be trimmed if necessary and further anchors, such as one or more sutures can be used to secure the device 88 within the fistula at one or more suitable locations, if desirable.

In certain embodiments, illustrative graft products can be used in conjunction with a suitable sealant or sclerosing solution which can be injected into a fistula tract or any side branches extending from the main fistula tract. Illustratively, for example, one or more sclerosants can be injected or otherwise placed within a tract either before or with the emplacement of an illustrative ECM graft construct so as to initiate a healing response to promote the ingrowth of patient tissue within the remodelable graft construct. Several possible sealants are known in the art as well as discussed above, and can include fibrin glue, such as Tisseal (Baxter Inc.). The glue can be prepared by mixing coagulation activation factors with fibrinogen, which then can react to form fibrin. The fibrin can form a matrix which can serve as a scaffold for tissue in growth, thereby promoting the closure of the fistula tract. For more information concerning the closure of branch fistulae that can be useful in certain embodiments of the present invention, reference can be made, for example to U.S. Pat. Pub. No. 2005/0070759 and/or U.S. utility patent application titled "Implantable Graft to Close a Fistula," filed on Jan. 21, 2005 ("Express Mail" Mailing Label No. EV 314 907 725 US).

In the event that multiple fistulae are present, an illustrative fistula graft of the invention can be inserted into each fistula tract, until all the primary openings are filled or otherwise closed. Identification of each fistula tract can be made using any suitable means, such as fistuloscopy, whereby each fistula tract, as well as the primary opening, can be accurately identified. In the event a complex fistula is present, a graft construct having one head and two or more tails can be inserted within the complex fistula using techniques discussed herein in order to treat and close the complex fistula. In certain embodiments, a flowable remodelable material, as discussed below, can be used either alone or in conjunction with one or more graft bodies in the treatment of a complex fistula.

Devices of the invention can be of sufficient dimension to fill at least the primary opening of a fistula and optionally extend to close the entire fistula tract, either alone or in combination with other similar or differing devices. In certain embodiments, the fistula plug will have a length "L" of at least about 0.20 cm, and in many situations at least about 1 to 20 cm (approximately 1 to 8 inches). In illustrative embodiments, the plug will have a length of from about 2 cm to 5 cm, or alternatively, from about 2 inches to 4 inches. Additionally, in certain embodiments, fistula plugs will have a diameter of from about 0.1 mm to 25 mm or more preferably from about 5 mm to 10 mm at the head of the plug, which can then taper to a tail having a diameter of from about 0.5 mm to 3 mm.

Additional embodiments of the invention provide methods for treating fistulas that involve the use of flowable remodelable extracellular matrix material. In such embodiments, the flowable material can be used to fill openings and/or tracts of fistulas, including anorectal or other alimentary fistulas, and promote tissue ingrowth to close the fistulas. In this regard, the flowable material can be delivered in any suitable fashion, including for example forcible ejection from cannulated members such as catheters, sheaths, or needles. Suitable flowable, remodelable ECM materials for use in this aspect of the invention can be prepared, for example, as described in U.S. Pat. Nos. 5,275,826 and 5,516,533 or in International Publication No. WO2005020847 (Cook Biotech Incorporated) published Mar. 10, 2005, which are each hereby incorporated by reference in their entirety. Such flowable materials can include solubilized and/or particulate ECM components, and in preferred forms include ECM gels having suspended therein ECM particles, for example having an average particle size of about 50 microns to about 500 microns, more preferably about 100 microns to about 400 microns. The ECM particulate can be added in any suitable amount relative to the solubilized ECM components, with preferred ECM particulate to ECM solubilized component weight ratios (based on dry solids) being about 0.1:1 to about 200:1, more preferably in the range of 1:1 to about 100:1. The inclusion of such ECM particulates in the ultimate gel can serve to provide additional material that can function to provide bioactivity to the gel (e.g. itself including FGF-2 and/or other growth factors or bioactive substances as discussed herein) and/or serve as scaffolding material for tissue ingrowth. Flowable ECM materials can also be used in conjunction with graft body devices as described herein, or implant bodies having other constructions. Implanted bodies can, for example, be provided at one or more locations of the fistula, e.g. within the primary opening, and can act as a confining barrier to an amount or bolus of flowable ECM material introduced against the barrier, such as in between two implanted graft bodies, and filling the tract of the fistula to promote healing.

Additionally, in certain embodiments, plug grafts of the invention can incorporate an effective amount of one or more antimicrobial agents or agents otherwise useful to inhibit the population of the graft construct or surrounding tissue with bacteria or other deleterious microorganisms. Illustrative such agents can include, for example, silver compounds, such as silver salts (e.g. silver sulfate), dextran, chitosan, chlorhexidine, and/or nitric oxide donor compounds. In illustrative embodiments, such agents can be incorporated throughout the plug graft constructs and/or on surfaces and/or selected regions thereof. These or other similar therapeutic agents, e.g. any drug, such as an antibiotic, can be incorporated directly on or in the graft constructs of the invention, or they can be incorporated with a suitable binder or carrier material, including for instance hydrogel materials. In this regard, the graft construct can serve to release the one or more agents over time so as to treat the tract during healing.

Additionally, in certain embodiments, illustrative graft constructs of the invention can be formed by randomly or regularly packing one or more pieces of single or multilayer ECM sheet material within a mold and thereafter processing the packed material. Such suitable processing can include, for example, providing the packed ECM sheet material in a partially or otherwise completely wetted or hydrated form and can complete, at least in part, by partially or completely dehydrothermally bonding the hydrated packed sheet material to establish a substantially unitary graft construct. Illustratively, for example, a randomly packed graft construct can be formed by placing folded, wadded, gathered, or otherwise packed ECM sheet material within a mold, and thereafter drying the randomly configured material to form a substantially unitary graft construct. In alternative embodiments, a packed graft construct can be formed by situating randomly packed hydrated ECM material within a substantially uniform ECM sheet material, for example a tubular or planar sheet material lining all or part of a mold, and thereafter processing the configured material to form a substantially uniform construct. Illustratively, for example, the outer surface of the graft construct can be either completely or partially covered or formed using an organized material, such as one or more layers or segments of ECM sheet material. In certain embodiments, the outer surface of a packed graft construct, or portions thereof, can be varied, for example, by selectively covering only portions of the randomly packed or positioned material with an ECM sheet material. Illustratively, a packed construct can be formed by either partially or completely covering the inner surface of a mold with one or more wetted ECM sheet materials, and filling the mold cavity with wadded or gathered wetted ECM material, and thereafter drying the positioned material using any suitable drying technique as discussed herein.

Illustratively, wetted randomly or regularly packed ECM materials of the invention can occupy any suitable configuration, shape, and/or length, as disclosed herein in the Figures or otherwise, and can be dried using any suitable drying technique or any suitable combination thereof, as disclosed herein. For example, in certain embodiments, the ECM material can be packed within a mold, as discussed above, and then dried within the mold. Alternatively, the ECM material can be packed within a mold and thereafter removed from the mold and dried. Still alternatively, a piece or pieces of ECM material can be packed within a mold, pressed or compressed within the mold, and thereafter dried, optionally while contained within the mold.

Randomly packed and regularly packed graft constructs of the invention can be desirable for use in certain embodiments of the present invention. For example, illustrative randomly or regularly packed graft constructs can have a somewhat tortuous or convoluted outer surface, depending on factors such as the amount and extent of wadding or folding that is present at the surface of the construct, the surface of the mold, and the density of the packing. These convoluted surfaces can provide increased surface area, which in turn, can provide additional area or sites for the binding or other retention of certain therapeutic agents, e.g. those disclosed herein, to the graft construct. Additionally, the overlapping material configuration that can be present within the body of an illustrative packed graft construct can minimize the number of longitudinal tissue planes that exist within the graft's body. Reduced longitudinal tissue planes within the construct's body can desirably reduce or prevent the flow of material through the construct, such as to enhance the independence of the rectal cavity from the soft tissue of the perianal region.

Packed, molded graft constructs of the invention can also include suitable flowable, comminuted, and/or sponge form materials, each of which can be ECM based, interspersed within rolled, folded, or otherwise randomly packed and/or covered ECM material. Additionally, these materials can be formed into any suitable shape, configuration, size and/or length as disclosed herein.

Figure 16:
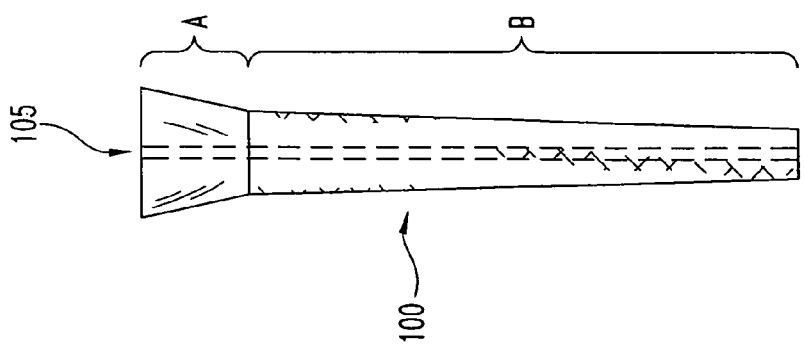
FIG. 16 depicts a perspective view of an illustrative medical product of the invention.

Additionally, in certain embodiments, graft constructs of the invention can include a hole or lumen that extends longitudinally through the construct, including partially or completely along the construct, such as through the cross-sectional center of the device (see e.g. FIG. 16). Such a lumen can be formed during the processing of material, such as by rolling a wetted ECM material around a mandrel or other elongate body, processing the material to provide a substantially unitary body (e.g. by molding and drying) and thereafter removing the mandrel or other elongate body. Such a lumen can be created by boring the lumen from an otherwise unitary graft construct, such as with a suitable gauged needle or the like. In certain embodiments, the graft lumen can be used to assist or enhance the placement of the construct within a fistula, such as by advancement over an elongate delivery device such as a wire guide. In alternative embodiments, the lumen can be used to contain and deliver a suitable therapeutic agent, such as disclosed herein, into the fistula tract and/or surrounding tissue, such as after and/or during emplacement of the graft construct within a fistula tract. Still alternatively, such a lumen can be used to infuse a therapeutic agent into the interstitial spaces of the graft construct, such as by plugging one end of the lumen followed by the infusion of the agent into and through the graft construct through the lumen.

In certain partial-lumen embodiments as discussed above, a plug device can include a longitudinal lumen that extends through only a portion of the device, such as beginning either at the head or tail of the device and exiting at a point on the outer wall of the device. Such a partial lumen can be used for receiving a wire guide. In one delivery procedure, such a plug device can track through the fistula over a previously located wire guide so as to become emplaced within the patient.

In additional aspects, the present invention provides implantable graft constructs having a plurality of passages formed or otherwise occurring therein, wherein each of the passages includes a generally coherent passage wall. These graft constructs may exhibit any suitable size, shape and configuration for treating fistulae or other bodily openings or passageways, and may also be comprised of one or more of a variety of biocompatible materials including any of those described herein. Illustratively, an inventive construct may be comprised of a collagen-containing material (e.g., an ECM material such as porcine small intestine submucosa), and include an elongate body having either a constant or varying cross-sectional area along its length, for example, a generally cylindrical elongate body or a body having a tapered portion. Also, as discussed in more detail below, some elongate graft bodies of the invention can have one or more lumens extending at least partially longitudinally through the bodies along their length. When utilized in the invention, such graft body lumens can exhibit any suitable size, shape and configuration within the graft body, and may or may not be in communication with one or more of the plurality of passages occurring in the graft body. Additionally, such a plurality of graft body passages may include any suitable number of individual passages positioned randomly or non-randomly in the graft body, wherein each of these passages can exhibit any suitable size, shape and configuration.

Further in this regard, any passage in a graft body can extend through all or a portion of the graft body, and in some forms, one or more passages extends from a graft body surface and includes a generally coherent passage wall. Illustratively, a graft body having an internal lumen can have passages extending partially or entirely through a wall of the tube, e.g., from an exterior surface to an interior surface of the wall of material defining the lumen. Also, the spacing and size of a passage in a graft body relative to another passage in the body, as well as the depth to which a particular passage extends into a graft body, can vary. In some forms, the passages are generally cylindrical voids, e.g. having diameters ranging from about 0.05 mm to about 15 mm, more typically from about 0.10 mm to about 5 mm, and even more typically from about 0.1 mm to about 1.0 mm. These and other graft body passages useful in the present invention can be spaced any suitable distance from one another, and in some embodiments, are positioned in a particular pattern (e.g., in rows), although a plurality of passages can be randomly placed as well. Further, a plurality of passages in a construct can be configured so that any one passage extends the same or a different distance into the construct relative to any other passage in the construct.

Inventive graft bodies having a plurality of passages occurring therein may be formed in any suitable manner. In some embodiments, passages can be created in a graft body after the graft body is formed, e.g. after a cast collagenous material is dried to form a coherent body. In some embodiments, at least part of the formation of some or all of the passages in a graft body occurs during formation of the graft body. Illustratively, an inventive method can include a step where a passage is initially provided in a hydrated material mass, e.g. by displacing a volume of material in the mass. Then, with the passage(s) present in the hydrated material mass, the mass can be subjected to suitable drying conditions (e.g., a lyophilization step) to cause or allow the passage to be retained in the dried graft body. It should be noted that a hydrated material in such processes (e.g., a reconstituted or naturally-derived collagenous material) can have any suitable level of hydration including full or partial hydration, and in this regard, a drying process can be used to lower starting material hydration to any suitable level including substantially dehydrated.

A volume of material can be displaced in a hydrated mass of material to create passages in any suitable manner, and in certain aspects, this is accomplished by forcing or otherwise introducing an implement or other material-displacing object (e.g., a cannulated or non-cannulated needle) into the mass. Other suitable material-displacing objects can be selected according to the type of passage desired.

Additionally, these and other inventive graft body formation methods can involve manipulating graft material within a mold or form. It should be noted that the graft material may or may not be hydrated when placed in, on, around, etc. a mold or form. For example, in some methods, a substantially dry ECM material (e.g., a powder or sheet material) can be placed in a mold and then suitably hydrated for further processing. In other methods, a hydrated starting material is placed in and/or on a mold or forming structure for further processing. For example, one or more hydrated sheets of ECM material can be applied to a form, e.g., wrapped at least partially around a mandrel so that portions of the sheet(s) overlap. Then, the one or more sheets can be dried, and in some embodiments, dried while under compression, to form a unitary graft construct. In some modes of operation, a hydrated graft material is provided within a single- or multiple-part mold having a plurality of apertures or holes extending through a wall of the mold, thereby providing access to the mold interior from an external location. These apertures can serve to enhance drying of a hydrated material during a processing step and in processes exerting vacuum pressure at these apertures, can promote and/or facilitate formation of surface protuberances on the graft material as portions of the same are drawn toward the apertures while under vacuum. In one aspect, an amount of ECM material is retained in such a mold, and needles or other material-displacing objects are inserted through some or all of the mold apertures and a distance into the ECM material, thereby displacing volumes of the ECM material. This can be performed when the graft material is hydrated, partially hydrated or dehydrated. In some forms, with needles inserted in a hydrated ECM material and providing passages therein, the material is subjected to conditions (e.g., freezing and/or dehydrating conditions) which, alone or in combination with one or more other conditions, cause or allow the passages to be generally retained in the ECM material after the needles are removed.

In one embodiment, one or more sheets of hydrated ECM material are suitably wrapped and/or randomly packed around a mandrel, and then a mold having a plurality of holes extending through a wall of the mold is placed around the material-covered mandrel, for example, so that an amount of pressure is placed on the ECM material. The mandrel can then optionally be removed. Thereafter, needles or other material-displacing objects are inserted through some or all of the holes and at least partially through the ECM material, thereby displacing volumes of the ECM material. The ECM material is then at least partially dried. In some aspects, a suitable lyophilization technique is employed, e.g., one with or without a pre-freezing step as described above. In these or other drying techniques in which needles or other penetrating elements are to be left within the mass during drying, they can optionally be provided with a plurality of apertures or holes or can otherwise be sufficiently porous to facilitate the drying operation by allowing the passage of gases from the wet mass. In one alternative embodiment, a hydrated ECM material with emplaced needles can be subjected to freezing conditions so that the material and any contained hydrate become substantially frozen. Thereafter, the needles can be removed from the ECM material, and the remaining construct (with the frozen material passages substantially retaining their shape) can be placed under a vacuum so that the frozen hydrant sublimes from the material, thereby resulting in a dry graft construct with retained passages therein.

In other modes of operation, passage-forming structures can be incorporated integrally into a mold so that passageways are formed upon introducing the starting material in and/or on the mold. In these aspects, the passage-forming structures can be part of the mold (e.g., extend from a surface of the mold), or they can be separate objects attached or otherwise coupled to the mold, to provide the desired passage or passages through the ultimately-formed graft body.

Figure 15A:
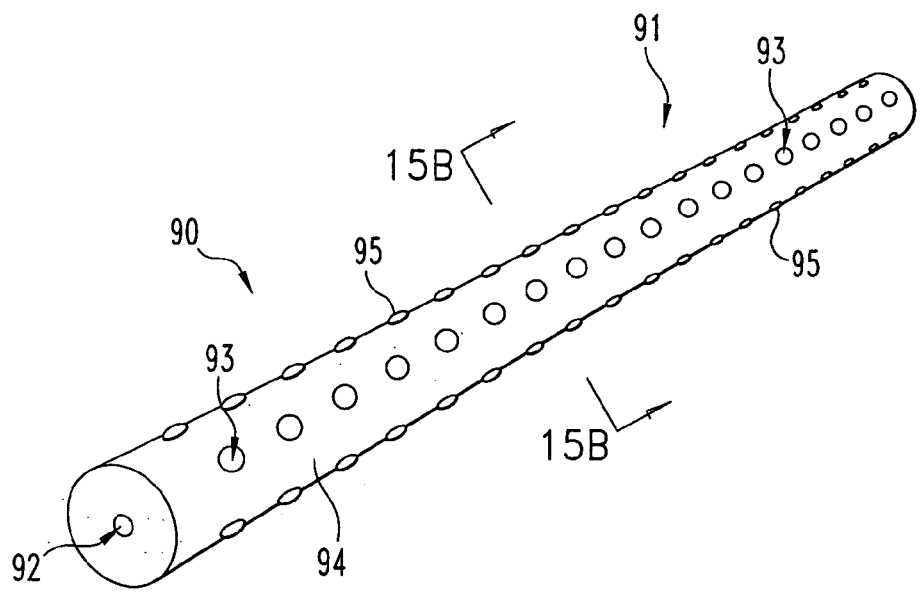
FIG. 15A shows a perspective view of another medical graft product of the invention.
Figure 15B:
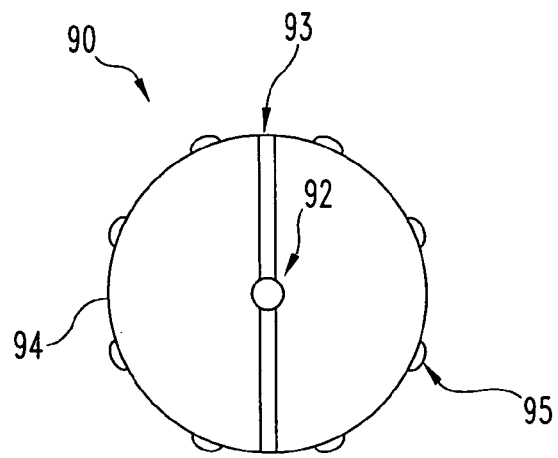
FIG. 15B provides a cross-sectional view of the medical graft product of FIG. 15A along the view line 15B-15B shown in FIG. 15A.
Figure 17B:
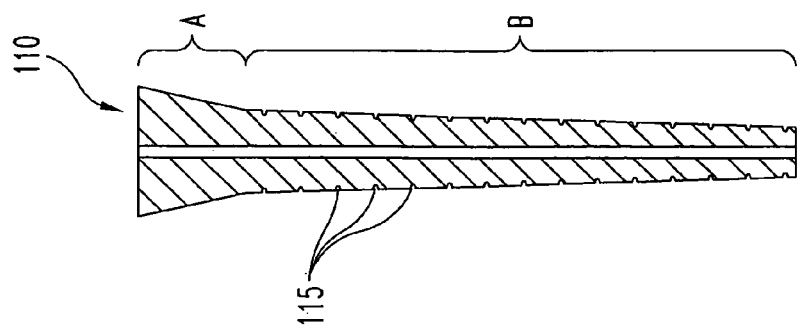
FIG. 17B depicts a cross-sectional view of the medical product depicted in FIG. 17A.
Figure 17A:
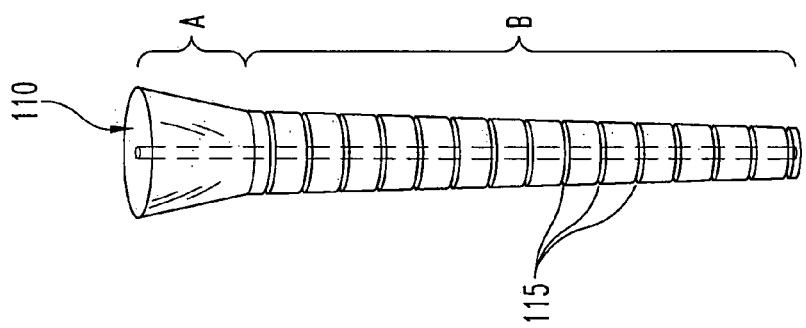
FIG. 17A depicts a perspective view of an illustrative medical product of the invention.

FIGS. 15A and 15B depict a dried, implantable graft construct 90 in accordance with the present invention. Graft construct 90 is comprised of an ECM material (e.g., porcine SIS), and includes an elongate graft body 91 having a lumen 92 extending through the construct along its length. Graft body 91 is slightly tapered toward one end, and has multiple passages 93 occurring therein. Passages 93 are spaced evenly apart along the length of graft body 91, and the longitudinal axis of each passage runs through (and perpendicular to the longitudinal axis of) graft lumen 92 to allow communication between opposing sides of a graft body exterior surface 94. Graft body 91 also has multiple surface protuberances 95 extending out from exterior surface 94.

Although not necessary to broader aspects of the invention, in some aspects, the formation of such a graft construct comprises wrapping one or more sheets of hydrated graft material around a mandrel a number of times. The resulting roll of graft material is then introduced into a mold, e.g. before or after withdrawing the mandrel from the roll. Thereafter, multiple material-displacing objects such as but not limited to needles are forced through apertures in the mold and into the hydrated graft material, and the material is subjected to one or more drying techniques such as a lyophilization process. In other aspects, the formation of such a graft construct includes placing a flowable graft material into a mold and then subjecting the graft material to further processing. For example, a flowable ECM material mass, such as a gel, paste or putty, potentially incorporating a particulate ECM material, can be placed into a mold, and then with volumes of material displaced in the mass (e.g. by penetrating needles), the ECM material can be dried or otherwise caused to form an integral piece to form a graft body having passages therein. Illustratively, each of the passages 93 can be provided by forcing a single object through the material mass, or alternatively, where a mandrel is left in place to form a longitudinal lumen, by forcing two objects into the mass and toward one another from opposed directions until they abut the mandrel. The mass can then be processed to a solid graft body as discussed herein.

With reference now to FIG. 16, an illustrative fistula plug 100 is depicted that has a central lumen 105 that extends through the plug 100 along the plug's longitudinal axis. As shown, the plug 100 can have two regions of differing porosity A, B, and the plug can occupy a generally conical shape. In certain embodiments, region A can be less porous than region B, e.g. so that region A can resist penetration or wicking of fluids from the rectal cavity when region A is implanted at a primary opening of an anorectal fistula. In other embodiments, region A may be more porous than region B, for example to enhance tissue infiltration at region A and/or to enhance a compressible character of region A, e.g. to facilitate healing of tissues at a primary fistula opening plugged with region A and/or a wedging, sealing engagement of region A with a primary fistula opening. The varied porosity of the material regions A and B can be provided in any suitable manner, including any of those described herein.

With general reference now to FIGS. 17 through 21, shown are additional devices of the present invention. In certain constructions of the illustrated devices, the structural features can provide strain relief and longitudinal flexibility within devices so as to resist device migration that can be caused by stress and strain associated with patient movement, e.g. walking, standing up/sitting down, exercise, etc. For example, FIGS. 17A and 17B depict a generally conical medical product 110 having a plurality of circumferential cuts 115 in the surface of the device, wherein the cuts are provided at spaced locations along the length of the device. Illustratively, the spacing, depth and/or width of each cut or of only certain cuts along the device can be varied, e.g. every third cut, in order to enhance the amount of stress relief that is provided by the device. In another embodiment, the circumferential cut can be arranged as a continuous spiral cut along some or all of the length of the device, and the pitch, depth, and/or other features of the spiral cut can be varied to control the additional flexibility provided to the device. Multiple, separate spiraling cuts can also be used along the length of the device to control the flexibility thereof. The cuts in these or other similar embodiments can, for example, be introduced during formation of the device body or can be imparted after its formation with a suitable tool such as a scalpel, razor blade, or other sharp cutting instrument. In certain desired embodiments, the cuts will be effective to increase the flexibility of the device but will leave the device with sufficient strength and toughness to be pushed or pulled through a fistula track without breaking.

Figure 18:
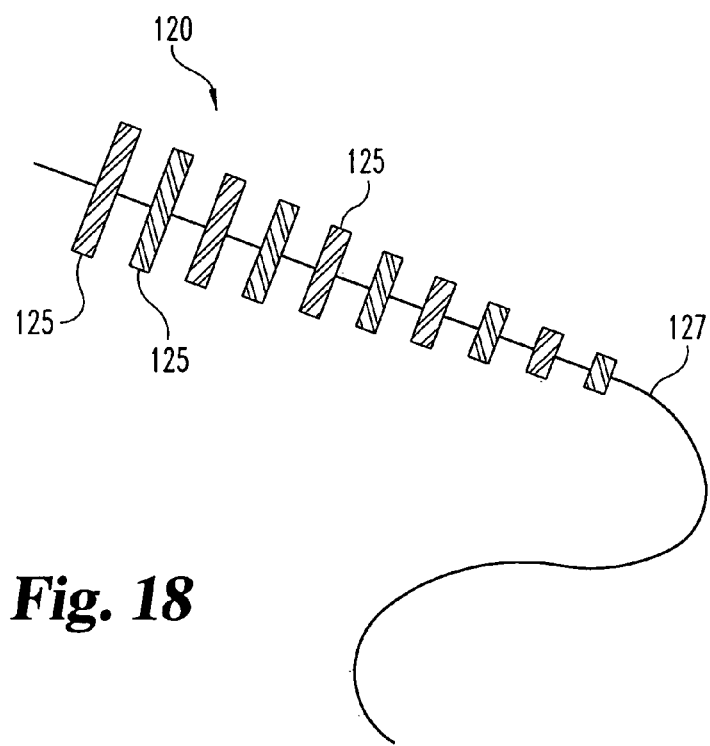
FIG. 18 depicts a perspective view of an illustrative medical product of the invention.

Turning now to FIG. 18, an illustrative medical device 120 is depicted that include a plurality of e discs 125 mounted on a resorbable thread or suture 127. The diameter of each disc 125 along the thread 127 can continuously vary such that a graft device 120 occupying a conical shape is formed. The distance between each disc, as well as the size of each disc, can be varied in order to provide varying degrees of strain relief to the device. In additional embodiments, the diameter of the discs can randomly vary, such as by alternating between large diameters and smaller diameters, and in certain embodiments the discs can be fused together to form a unitary construct. When emplaced within a patient, the threadably attached discs can be forcibly deformed to contact one another within the tract so as to unify into a generally continuous graft, or alternatively the discs in the implanted configuration can remain spaced from one another. In other device embodiments, the illustrated discs can be replaced by graft elements having other suitable shapes, sizes and/or forms, e.g. cups, bowls, hemispheres, spheres, cones, and the like.

Figure 19:
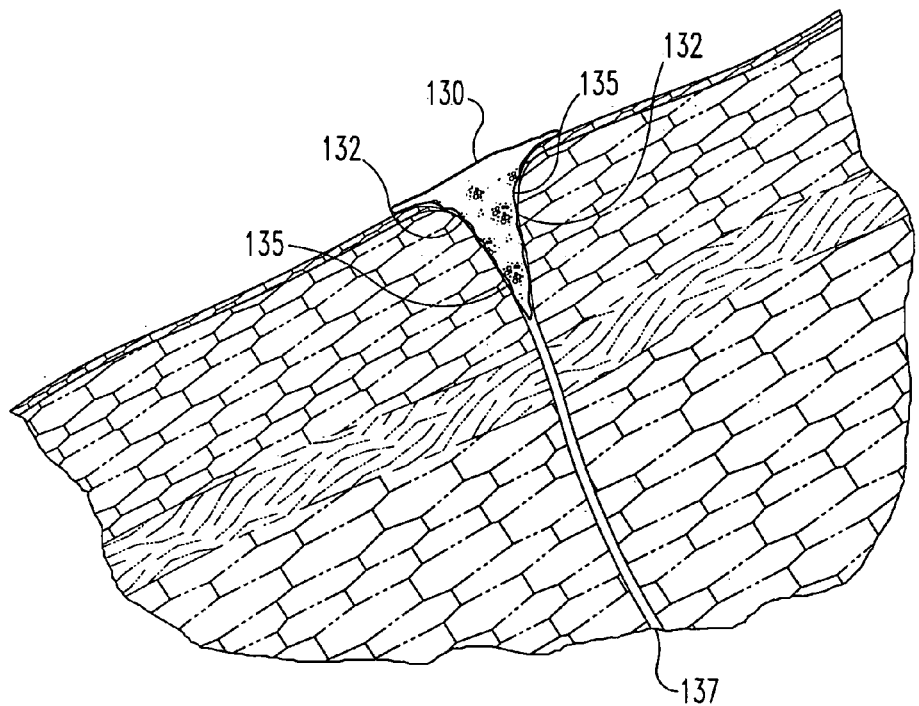
FIG. 19 depicts an illustrative grafting procedure of the invention.

With reference to FIG. 19, an illustrative graft emplacement is depicted showing an expandable plug device 130 having a plurality of bulges 132 and reliefs 135 that is implanted within the primary opening of a fistula tract 137. The bulges 132 and reliefs 135 can occur in a generally symmetrical fashion along the length of the plug 130 and can serve to help secure the device within the primary opening over time. The plug device 130 can be differentially dried such that the head region occurring at the primary opening occupies a more closed matrix structure than the tail. The diminished porosity of the head region can provide a separation between the alimentary canal and the fistula tract 137, which will enhance the closure of the tract 137. In additional embodiments, the tapered portions of the plug's 130 exterior surface near the head of the plug, or otherwise, e.g. the entire plug surface, can be coated with a suitable sealant or adhesive, e.g. a fibrin glue, in order to promote the separation of the tract from the alimentary canal and/or help secure the plug 130 within the primary opening. In still additional embodiments, one or more sutures can be used to anchor the head of the plug to surrounding patient tissue to provide securement to the plug 130, or in alternative embodiments, the expandable nature of the plug will provide sufficient securement of the device within the primary opening such that additional securing means, e.g. adhesive, sutures, are not required, but still may be desirable.

Figure 20:
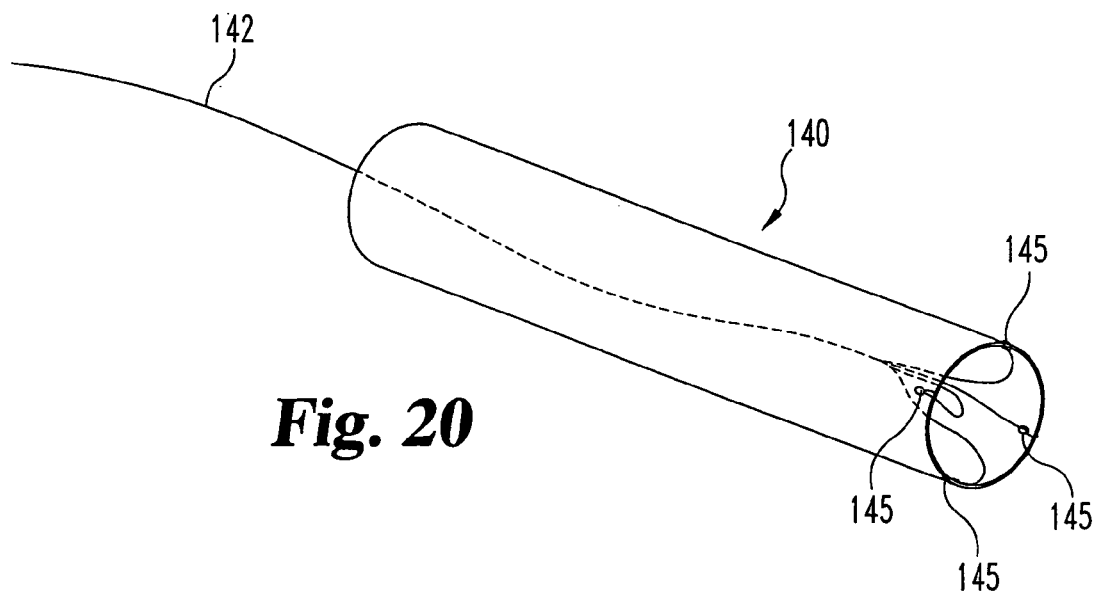
FIG. 20 depicts a perspective view of an illustrative medical product of the invention.
Figure 21:
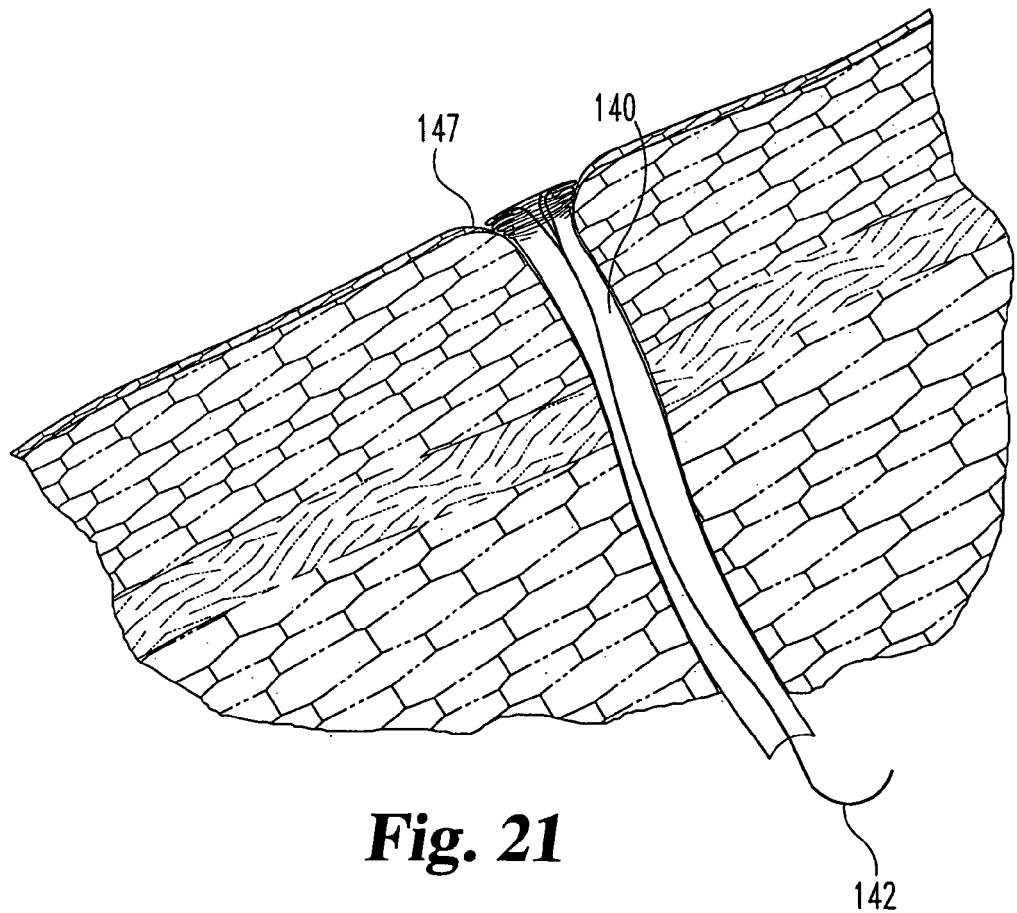
FIG. 21 depicts and illustrative grafting procedure of the invention.
Figure 22:
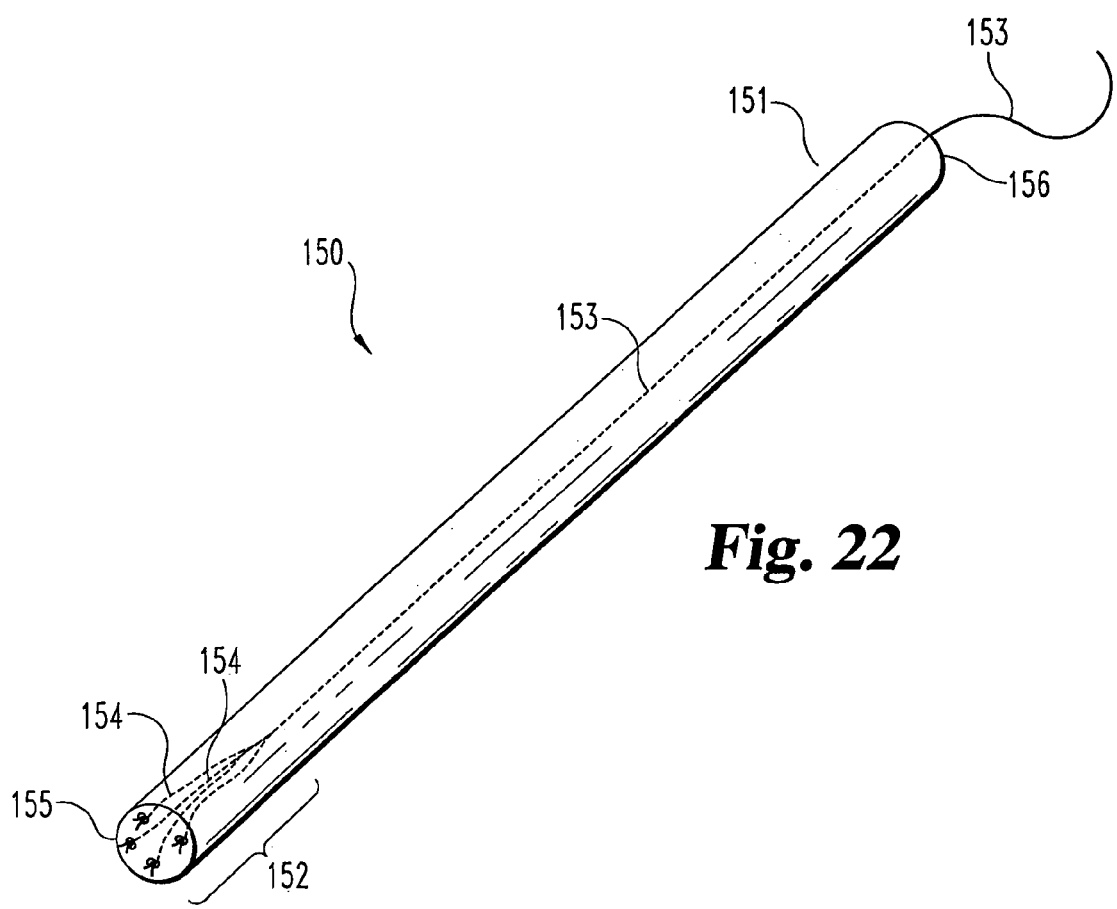
FIG. 22 depicts one embodiment of a graft of the invention.
Figure 23:
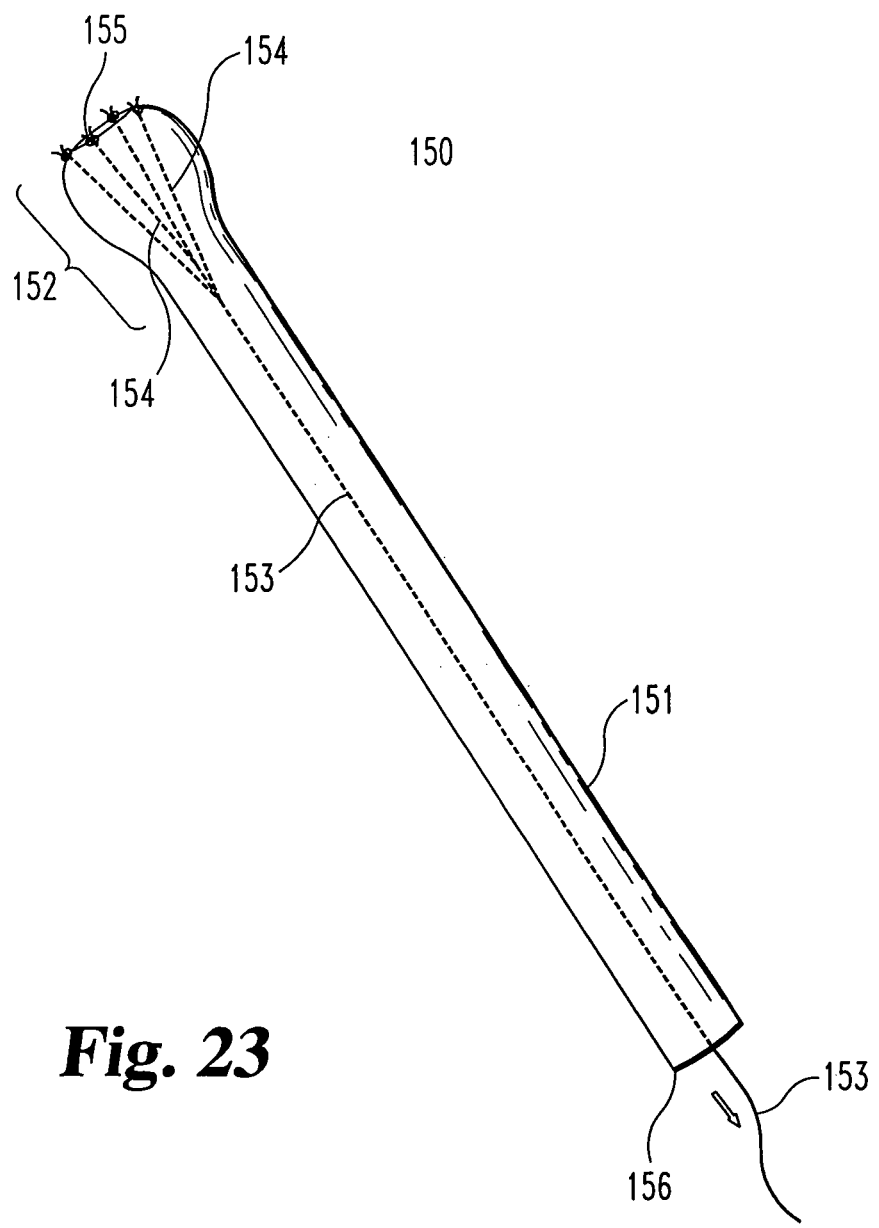
FIG. 23 depicts the graft of FIG. 22 in use.

With reference now to FIG. 20, an illustrative device is shown that includes a relatively flexible remodelable or resorbable tube 140 and a suture web 142 or other pulling tether that is connected to the distal end of the tube 140 at four locations and that extends proximally through the tube lumen beyond the proximal end of tube 140. In alternative embodiments, the suture web can be connected at more or less than four locations, can connect at any suitable location (s) along the length of the tube, and may or may not unify at any location within or proximal to the tube lumen, including having a plurality of sutures that separately extend from the proximal end of the tube. As shown in FIG. 21, the tube 140 can be located within a fistula tract and the suture web 142 can thereafter be pulled (from an external location) in a proximal direction so as to collapse and gather or bunch the distal end of the tube within the primary opening 147 of the fistula tract so as to close the primary opening. In this regard, the wall thickness of the tube can be varied in order to vary the collapse/gather characteristics of the graft material at the primary opening. For example, the tube may be a solid cylindrical device having a relatively small lumen therethrough for receiving the suture or other tether, thus providing more abundant material to gather within the primary opening when the tether is pulled. In illustrative embodiments, the distal end of the tube can be sutured to patient tissue, and the thread and proximal tube end can be trimmed and optionally secured to the patient. The flexible nature of the tube will allow the tube to collapse and gather within the primary opening 147, potentially in a fashion which effectively seals the tube 140 at the primary opening. In certain embodiments, one or more therapeutic agents can be introduced into the lumen of the implanted tube and/or additional graft material, such as a flowable graft material, can be placed within the lumen so as to enhance the closure of the tract. In alternative embodiments, the tube lumen extending along the fistula tract can be left open and can serve to facilitate drainage of the lumen during healing. In still further alternative embodiments a fistula closure device with an actuatable end can include an elongate body (e.g cylinder) of graft material having a longitudinally-collapsible distal region and an internal or external tether attached to the distal region and extending proximally along the body and configured such that pulling the tether in the proximal direction collapses the distal region, causing an enlarged diameter thereof. Illustratively, FIG. 22 provides a perspective view of a graft device 150 including a plug body 151 having collapsible distal region 152 and an internal pull tether 153. Internal pull tether 153 has multiple distal attachment portions 154 exiting the distal end 155 of body 151 and engaged at distributed locations on distal end 155, for instance with knots as shown. Other engagement members such as beads, discs, clips, etc., desirably resorbable, can also be used. Pull tether 153 extends through the body 151 and exits proximal end 156 thereof. As illustrated in FIG. 23, when implanted within a fistula tract with collapsible region 152 near, at or beyond a primary opening thereof, tether 153 can be pulled to collapse distal region 152 and cause an expanded diameter thereof that can lodge within, or can be positioned to lodge within, the primary opening. The distal and proximal ends of the device 150 can then be secured to patient tissue by suturing or other techniques if desired, as described herein.

In certain aspects, fistula plug devices can include elongate tubular balloon structures which can be placed within at least the primary opening of the fistula so as to provide for the closure of the fistula. Such elongate tube structures can have a closed distal end, a lumen, and an open proximal end. The distal end of the tube structure can reside in the secondary opening, but it will typically be more desirable to locate the closed distal end within the primary opening of the fistula tract. In certain aspects, the elongate tubular structure can be expandable with a fill material so as to expand within the fistula and provide closure thereof. Such expandable constructs include both single walled and double walled balloon devices. Such double walled balloon devices generally contain two lumens. The first lumen is defined by the outer balloon wall and the inner balloon wall, and the second lumen is defined by the inner balloon wall. Additionally, the elongate tube structure can include a remodelable material and can be filled or inflated with a remodelable fill material, such that the patient's tissue remodels the device and fill material to enhance the closure of the fistula tract.

Turning now to a discussion of elongate tube materials, any suitable biocompatible material can be used to form the tube, as are discussed herein, such as remodelable materials, e.g. absorbable synthetics or extracellular matrix materials, or non-absorbable synthetic materials, including those described herein. In certain aspects, suitable elongate tube materials can be obtained by isolating tubular or pouch form ECM materials, such as, for example, small stomachs, urinary bladders, vascular vessels, ureters, and/or suitable portions of the gastrointestinal (GI) tract. Other suitable elongate tube or balloon materials may include substantially non-antigenic elastic materials. For additional information as to suitable balloon materials that can be used in the present invention, reference can be made, for example, to U.S. Pat. Nos. 4,819,637, 5,222,970, 5,304,123, 5,411,475, 5,779,672, and/or 5,830,228 each of which is hereby incorporated by reference in its entirety.

The elongate tube may include one or more radiopaque and/or ecogenic markers or a radiopaque coating or impregnation to assist in visualization of the material during a non-invasive procedure. For example, radiopaque substances containing tantalum, barium, iodine, or bismuth, e.g. in powder form, can be coated upon or incorporated within the ECM or other remodelable material, such that, for example, the location of the balloon's distal end is detectable.

Turning now to a discussion of inventive fill materials that can be used in conjunction with balloons or other fillable devices, the device can be filled with any material conducive to achieving closure of a fistula of interest. In this regard, the fill material may be a solid, liquid, gel, or foam, such as blood, polymer, contrast medium, a remodelable or bioabsorbable material, saline, a non-bioabsorbable material, collagen rods or particulates, a collagenous or gelatinous foam, air, chitosan, gelatin, oxidized regenerated cellulose, calcium alginate, alginate, thrombin-fibrin enhanced materials, fibrin glues, or any suitable combination thereof.

In one embodiment, the fill material can comprise a comminuted, flowable, (e.g. fluidized), and/or gel form material, as discussed herein. Such fill material can include one or more agents for contacting the fistula tract through pores or apertures present in the elongate tube. Illustrative such agents include sclerosive agents, aqueous based agents, e.g. hydrogen peroxide or saline, antibiotics, or any suitable combination thereof. Alternatively, the fill material can comprise a suitable solidifying polymer, such as a polymer of 2-hydroxyethyl methacrylate (HEMA). Upon addition of a catalyst to HEMA at a certain temperature, HEMA will gradually change from a liquid form to either a gelatinous or solid form over approximately twenty minutes. This change in form is desirable in a fill material because the material can easily flow into the elongate tube device, eliminating void space between the device and patient tissue, and then solidify, thereby enhancing the closure of the fistula. For more information on HEMA and other fill materials useful in embodiments of the present invention, reference can be made, for example, to U.S. Pat. Nos. 4,819,637, 5,222,970, 5,304,123, 5,411,475, and/or 5,830,228, each of which is hereby incorporated herein in its entirety.

Additionally, the fill material, including, e.g. remodelable ECM fill materials, can include one or more radiopaque and/or ecogenic markers or a radiopaque coating or impregnation to assist in visualization of the material during a non-invasive procedure. For example, radiopaque substances containing tantalum, barium, iodine, or bismuth, e.g. in powder form, can be coated upon or incorporated within a fill material, such that, for example, the location of the fill material within a patient's body can be detected.

Elongate tube devices can have sufficient length to reside within the entire fistula tract, or only a portion thereof. Illustrative such lengths can typically range from about 0.5 cm to about 20 cm. Such lengths can often range from at least about 1 cm in length to about 10 cm in length. Further, an elongate tube device can be provided to a physician in a relatively long length and the physician can thereafter cut the device down to fit the length of the desired fistula tract. Illustrative such elongate tube structures can have maximum expanded diameters that range from about 1 mm to about 25 or more mm. In certain embodiments the diameter of the tube can be relatively constant along the tube. In certain other embodiments the tube diameter can vary along the length of the tube, such as to provide a device having a distal end that is wider than the proximal end. Such a device can provide a tapered region and optionally a continuous taper in a direction from the distal device end to the proximal device end so as to occupy a conical shape. For example, in certain forms the distal tube end can have a maximum expanded diameter of about 1-20 mm and the tail can have a maximum expanded diameter of about 0.1 to 5 mm. In additional embodiments, the distal maximum expanded diameter of the balloon can be such that a bulb is formed at the distal end of the device. Optionally, the bulbed device can thereafter continually taper down to the proximal tube end. Illustratively, the maximum expanded tube diameter can vary in any suitable manner along its length to provide a plurality of balloon shapes, e.g. bow tie shapes, elongate diamond shapes, and the like.

Such elongate tube devices can be delivered within the fistula using any suitable technique as discussed herein or otherwise. In certain embodiments, the elongate tube can be received over an elongate device, such as a fistula probe, pusher, or sheath, and thereafter be located within a fistula tract by moving the elongate device through the tract from the secondary opening to the primary opening so as to push the tube through the tract. After the device is located within the tract, it can optionally be filled or inflated using a suitable fill material as discussed herein. Fill can be added using any suitable technique or device, such as a syringe containing fill material. The fill material can be placed into the elongate tube directly from the syringe, or alternatively, the syringe can be hooked to a suitable cannulated device, such as a sheath or needle, and the fill material can flow through the device and into the elongate tube.

In one delivery mode for a tube graft device, a sheath can be placed within a fistula tract and the elongate tube can be placed within the sheath. The tube can be placed within the sheath before or after the sheath is located within the fistula. The sheath and balloon can be placed within the tract via either an approach from the secondary opening or an approach from the primary opening. Optionally, the sheath and/or tube can be emplaced with the assistance of a previously located wire guide.

Figure 24:
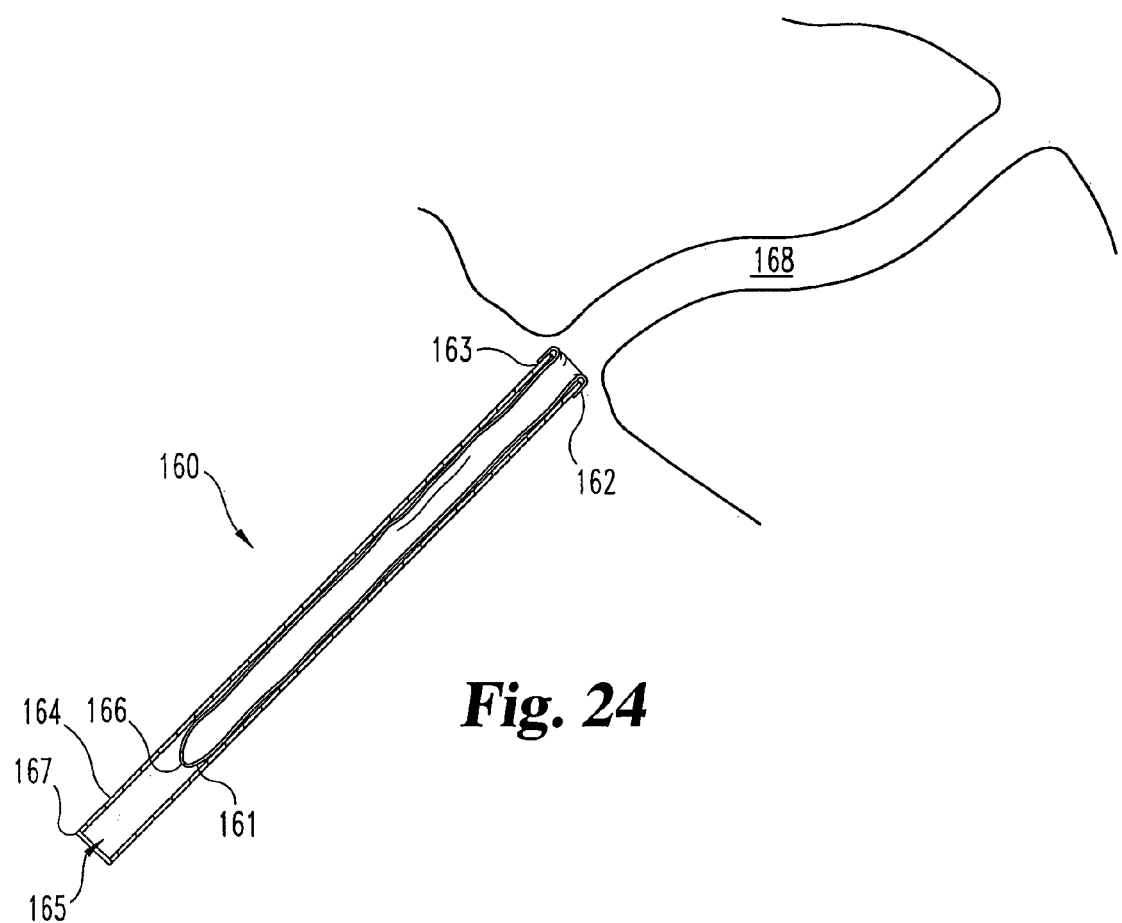
FIG. 24 depicts one embodiment of a balloon grafting apparatus of the invention.
Figure 25:
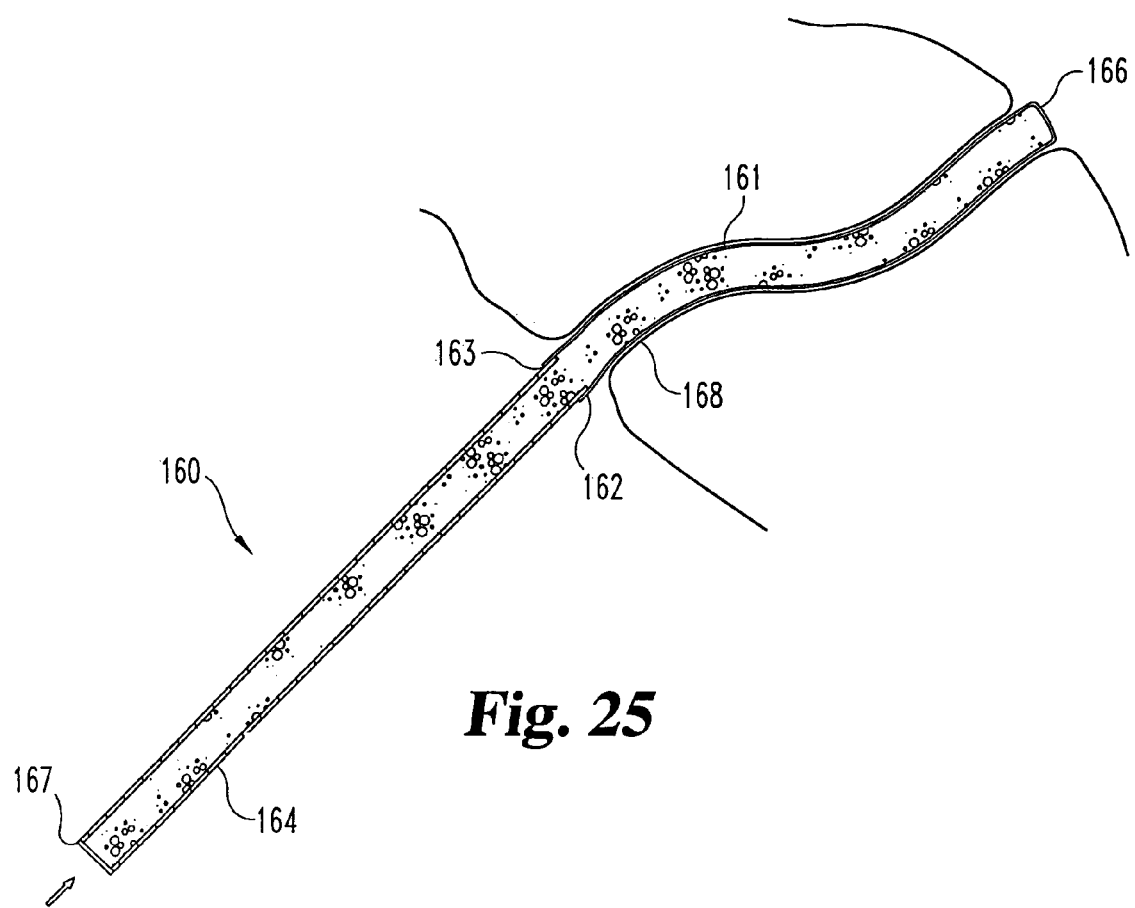
FIG. 25 depicts the apparatus of FIG. 24 in use.

In certain embodiments of the invention, a treatment system includes an elongate fillable balloon having a balloon opening associated with a lumen of a delivery device for delivering a fill material into the balloon. The delivery device can, for example, be a syringe having an outlet tube, or a catheter, sheath or similar cannulated device through which a fill material can be passed. In desirable embodiments, the balloon is received at least partially and potentially completely within the lumen of the fill material-delivery device, for example in a gathered and/or inverted configuration, and is partially or completely deployable from a distal lumen opening of the device upon passing a fill material into a proximal lumen opening of the device. For instance, the material defining the balloon opening can be secured to the exterior of the delivery device tube at or proximate to the distal end thereof, or to the walls of the delivery device lumen, leaving the balloon opening in an open position for receiving fill material passed through the delivery device lumen. As one illustrative embodiment, FIG. 24 shows balloon delivery apparatus 160 including a remodelable or resorbable balloon graft 161 having a proximal end 162 connected to the distal end 163 of a cannulated device 164, such as a sheath, having an internal lumen 165. A portion of the balloon graft 161 can be inverted within itself, and in certain embodiments, the bulk of the balloon 161 body, including the distal end 166, can be located within the sheath lumen. The distal end 163 of the cannulated device 164 can then be placed at (or within) the primary or secondary opening of a fistula tract, such as a fistula tract that has been prepared by one or more flushes of suitable solution, e.g. hydrogen peroxide. Thereafter, the balloon can be deployed within the fistula tract using any suitable technique to evert or deploy the balloon from the lumen of the sheath. One such technique includes the use of a rod or other elongate pusher element to move the balloon from the sheath lumen and extend it within the fistula tract. Alternatively or additionally, a fill material, such as a flowable remodelable or resorbable material can be passed distally through the lumen 165, such as by mounting a syringe containing fill material on the proximal end 167 of the cannulated device 164 with a luer lock system. Fill material can be forcibly added through the lumen 165 in a fashion that causes the balloon to eject from the distal end and elongate into and through a fistula tract 168 (see FIG. 25). The filling can be continued until the tube is sufficiently filled within the fistula tract so as to cause closure thereof. In certain embodiments, fill material can be added to the elongate balloon graft structure on more than one occasion, if desirable, such as during follow-up office visits.

Once the elongate tube is sufficiently emplaced within the tract, the proximal tube end can be closed. Illustrative closure devices or techniques, include tying off the tube and/or securing a closed tube end with fasteners, clips, absorbable sutures, and/or elastic cuffs. In preferred embodiments, the closure device or material will be at least absorbable, if not remodelable. As part of the closure process, the proximal tube end can be trimmed and optionally secured to patient tissue. The distal tube end can also be secured to patient tissue using any suitable technique discussed herein. In additional aspects, the tube can include one or more protuberances, barbs, and/or anchors, such as along its body to provide migration resistance to the device. For more information regarding inflatable tube devices that can be adapted to and useful in certain embodiments of the present invention, reference can be made, for example, to U.S. patent application Ser. No. 11/294,998, entitled "Inflatable Occlusion Devices, Methods, and Systems, filed on Dec. 6, 2005 and/or U.S. patent application Ser. No. 11/322,145, entitled "Inverting Occlusion Devices, Methods, and Systems, filed on Dec. 29, 2005, each of which is incorporated herein by reference.

The invention also provides medical kits that include graft devices of the invention sealed within medical packaging potentially in combination with other components, for example including one or more of a sheath, a guidewire, a fistula probe, etc. The final, packaged products are provided in a sterile condition. This may be achieved, for example, by gamma, e-beam or other irradiation techniques, ethylene oxide gas, or any other suitable sterilization technique, and the materials and other properties of the medical packaging will be selected accordingly.

All publications cited herein are hereby incorporated by reference in their entirety as if each had been individually incorporated by reference and fully set forth.

The use of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A medical graft product for treating a fistula having at least a primary opening and a fistula tract, the medical graft product comprising:
   an elongate plug body configured to fill at least a segment of a fistula tract, the elongate plug body comprised of a dried, remodelable collagenous material including a plurality of generally cylindrical passages formed therein prior to being lyophilized and the dried, remodelable collagenous material effective to promote cellular invasion and ingrowth into the remodelable material for closing the fistula with remodeled patient tissue, wherein each of the formed passages has a generally coherent passage wall that extends from an exterior surface of the plug body into interior regions of the plug body, the plurality of generally cylindrical passages being sufficient to provide an increased exposed surface area extending into the interior regions of the plug body such that the remodelable collagenous material in the plug body is substantially uniformly lyophilized.

2. The medical graft product of claim 1, wherein the collagenous material comprises a remodelable angiogenic extracellular matrix material.

3. The medical graft product of claim 2, wherein the remodelable angiogenic extracellular matrix material comprises submucosa.

4. The medical graft product of claim 3, wherein the submucosa comprises porcine submucosa.

5. The medical graft product of claim 3, wherein the submucosa comprises mammalian small intestine submucosa.

6. The medical graft product of claim 1, wherein the collagenous material comprises submucosa, dura mater, pericardium, basement membrane, or dermal collagen.

7. The medical graft product of claim 1, wherein at least one of the plurality of formed passages extends from a first plug body surface to a second plug body surface.

8. The medical graft product of claim 1, wherein the elongate plug body includes a generally cylindrical longitudinal body segment.

9. The medical graft product of claim 1, wherein the elongate plug body includes a generally conical longitudinal body segment.

10. The medical graft product of claim 1, wherein said elongate plug body is of a length sufficient to extend from the primary opening through the fistula tract and out a secondary fistula opening.

11. The medical graft product of claim 10, wherein said elongate plug body is from 3 to 15 cm in length.

12. The medical graft product of claim 1, wherein said elongate plug body comprises a rolled collagenous sheet material providing a volumetric body.

13. The medical graft product of claim 12, wherein the rolled sheet material provides spiral layers.

14. The medical graft product of claim 13, wherein the spiral layers are compressed and bonded so as to form a substantially unitary construct.

15. The medical graft product of claim 14, wherein the spiral layers are dehydrothermally bonded to one another.

16. The medical graft product of claim 1, wherein the collagenous material comprises a multilaminate material.

17. The medical graft product of claim 1, wherein the elongate plug body has a plurality of protuberances on an exterior surface of the plug body.

18. The medical graft product of claim 1, wherein the collagenous material comprises a sponge form material.

19. The medical graft product of claim 1, wherein the dried collagenous material includes a first region and a second region, wherein the first region and the second region are formed by differentially drying the collagenous material.

20. A medical kit including the product of claim 1 enclosed in sterile medical packaging.

21. The medical graft product of claim 1, wherein said generally cylindrical passages are elongate cylindrical passages.

22. A medical graft product useful for the treatment of a fistula having a primary opening, the medical graft product comprising:
an elongate graft body comprised of one or more pieces of compacted sheet-form remodelable extracellular matrix material defining contacting layer portions of the sheet-form extracellular matrix material;
wherein said contacting layer portions of sheet-form extracellular matrix material are sufficiently bonded to one another to provide said graft body as a substantially unitary structure; and
wherein the graft body includes a plurality of elongate cylindrical voids formed therein extending from an exterior surface of the graft body into interior regions of the graft body, the elongate cylindrical voids having diameters ranging from about 0.05 mm to about 15 mm; and
wherein the plurality of elongate cylindrical voids are formed prior to the graft body being lyophilized.

23. The medical graft product of claim 22, wherein the elongate graft body is from 3 to 15 cm in length.

24. The medical graft product of claim 23, wherein said one or more pieces of compacted sheet-form remodelable extracellular matrix material are substantially uniformly lyophilized.

25. The medical graft product of claim 22, wherein the elongate cylindrical voids have diameters ranging from about 0.10 mm to about 5 mm.

26. The medical graft product of claim 22, wherein the elongate cylindrical voids have diameters ranging from about 0.10 mm to about 1.0 mm.

27. The medical graft product of claim 22, wherein the extracellular matrix material comprises submucosa, dura mater, pericardium, basement membrane, or dermal collagen.

28. The medical graft product of claim 22, wherein the drying conditions cause the sublimation of frozen water.

29. A method for treating a fistula having at least a primary opening and a fistula tract, comprising:
providing a medical graft product according to claim 22; and
locating the elongate graft body within a fistula such that the body lodges within and fills at least a segment of the fistula tract.

30. The method of claim 29, wherein the graft body further comprises a head and a tail, and wherein a suture configured for anchoring extends past the tail.

31. The method of claim 30, wherein said locating further comprises:
placing the head of the graft body within the primary opening of an anorectal fistula, so as to place the tail of the graft body within a tract of the anorectal fistula; and
securing the graft body within the anorectal fistula.

32. The method of claim 31, wherein said securing comprises securing the body at a location that is at or external to a secondary fistula opening.

33. The method of claim 29, wherein the extracellular matrix material comprises submucosa, dura mater, pericardium, basement membrane, or dermal collagen.

34. The method of claim 29, wherein the primary opening is located in a wall of the alimentary canal.

35. The method of claim 29, wherein the fistula is an anorectal fistula.

36. The method of claim 29, wherein the extracellular matrix sheet material is an expanded extracellular matrix sheet material.

37. A medical graft product useful for the treatment of a fistula having a primary opening, the medical graft product comprising:
an elongate, lyophilized collagenous graft body comprising one or more pieces of compacted sheet-form remodelable extracellular matrix material arranged to define contacting layer portions of the sheet-form extracellular matrix material, with the contacting layer portions of sheet-form extracellular matrix material sufficiently bonded to one another provide the graft body as a substantially unitary structure; and
wherein the graft body includes a plurality of elongate cylindrical voids formed therein extending from an exterior surface of the graft body into interior regions of the graft body, the elongate cylindrical voids formed prior to the elongate collagenous graft body being lyophilized, and the elongate cylindrical voids sufficient to provide an increased exposed surface area extending into the interior regions of the graft body such that the extracellular matrix material in the graft body is substantially uniformly lyophilized.

38. The medical graft product of claim 37, wherein the graft body is from 3 to 15 cm in length.

39. The medical graft product of claim 37, wherein the elongate cylindrical voids have diameters ranging from about 0.05 mm to about 15 mm.

40. The medical graft product of claim 37, wherein the elongate cylindrical voids have diameters ranging from about 0.10 mm to about 5 mm.

41. The medical graft product of claim 37, wherein the elongate cylindrical voids have diameters ranging from about 0.10 mm to about 1.0 mm.

42. The medical graft product of claim 37, wherein the remodelable extracellular matrix material comprises submucosa.

43. The medical graft product of claim 42, wherein the submucosa comprises porcine submucosa.

44. The medical graft product of claim 42, wherein the submucosa comprises mammalian small intestine submucosa.

45. The medical graft product of claim 37, wherein the remodelable extracellular matrix material comprises submucosa, dura mater, pericardium, basement membrane, or dermal collagen.

* * * * *